United States Patent [19]

Rodman

[11] Patent Number: 5,606,026
[45] Date of Patent: Feb. 25, 1997

[54] NATURAL HUMAN IGM ANTIBODIES IMMUNOREACTIVE WITH THE TAT PROTEIN OF HIV-1

[75] Inventor: Toby C. Rodman, New York, N.Y.

[73] Assignee: The Institute for Human Genetics and Biochemistry, Geneva, Switzerland

[21] Appl. No.: 53,079

[22] Filed: Apr. 26, 1993

Related U.S. Application Data

[63] Continuation-in-part of Ser. No. 173,705, Mar. 25, 1988, abandoned, Ser. No. 873,917, Apr. 24, 1992, abandoned, Ser. No. 912,026, Jul. 9, 1992, abandoned, and Ser. No. 924,412, Jul. 30, 1992, abandoned.

[51] Int. Cl.$^6$ .................... C07K 16/00; C07K 16/08; C07K 16/44
[52] U.S. Cl. .................... 530/387.9; 530/389.1; 530/389.4
[58] Field of Search .................... 530/387.9, 389.1, 530/389.4

[56] References Cited

U.S. PATENT DOCUMENTS 4,699,877  10/1987  Cline et al. ..

OTHER PUBLICATIONS

Berneman et al., *Eur J. Immunol* 1992.22: pp. 625–633; 1992.
Martin et al., *J. Exp. Med. The Rockefeller University Press*, vol. 175; pp. 983–991; Apr. 1992.
Kasaian et al., *The Journal of Immunology*, vol. 148, pp. 2690–2702, No. 9; pp. 2690–2702; May 1992.
Turano et al., *Proc. Natl. Acad. Sci USA*, vol. 89, pp. 4447–4451; May 1992.
Algiman et al., *Proc. Natl. Acad. Sci USA*, vol. 89, pp. 3795–3799; May 1922.
Lerner et al., *Science*, vol. 258, pp. 1313–1314; Nov. 1992.
Citterio et al., *Transplantation Proceedings*, vol. 24 No. 2; pp. 437–438; Apr. 1992.
Calnan et al., *Genes & Development*, pp. 201–210; 1991.
Chen et al., *The Journal of Immunology*, vol. 147, pp. 2359–2367; Oct. 1, 1991.
Kang et al., *Proc. Natl. Acad. Sci. USA*, vol. 89, pp. 2546–2550; Apr. 1992.
Hammer et al., *Transplantation Proceedings*, vol. 24, No. 2; pp. 590–591; Apr. 1992.
Willoughby et al., *the New England Journal of Medicine*, vol. 325 No. 2; pp. 73–80; Jul. 1991.
Buckley et al., *The New England Journal of Medicine*, pp. 110–117; Jul. 1991.
McCune, *Cell*, vol. 63, pp. 351–363, pp. 351–363; Jan. 1991.
Avrameas, *Immunology Today*, vol. 12, pp. 154–162; May 1991.
Varela et al., *Proc. Natl. Acad. Sci.*, vol. 88, pp. 5917–5921; Jul. 1991.
Urlacher et al., *Clin. Exp. Immunol.*, vol. 83, pp. 116–120; 1991.
Zhang et al., *The Journal of Immunology*, vol. 145, pp. 2489–2493; Oct. 1990.
Pruslin et al., *Journal of Immunological Methods*, vol. 137, pp. 27–35; 1991.
Rodman et al., *Experimental Cell Research* 150, pp. 269–281; 1984.
Rodman et al., *J. Exp. Med.*, vol. 167, pp. 1228–1246; Mar. 1988.
Stenberg et al., *Journal of Immunological Methods*; pp. 3–15; 1988.
Rath et al., *Journal of Immunological Methods*; pp. 245–249; 1988.
Harlow et al., *Antibodies A Laboratory Manual*; pp. 283–317; 1988.
Griswold, *Journal of Immunoassay*, pp. 145–171; 1987.
Oss et al., *Molecular Immunology*, vol. 24 No. 7, pp. 715–717; 1987.
Paul, *Fundamental Immunology*, pp. 599–608; 1984.
Nieto et al., *Molecular Immunology*, vol. 21 No. 6, pp. 537–543; 1984.
Rodman et al., *J. Cell Biology*, vol. 80, pp. 605–620; 1979.
Rodman et al., *Gamete Research 8*, pp. 129–147; 1983.
Kolk et al., *Biochimica et Biophysica Acta*, pp. 307–319; 1975.
Karush, *Advances in Immunology*, vol. 12, pp. 1–40; 1962.
Steward et al., *Immunology*, vol. 23, pp. 881–887; 1972.
Bio Rad, Price List Q, Research Scale Chromatography Applications, pp. 107–109.
Bruni et al., *J. Theor. Biol.*, vol. 61, pp. 143–170; 1976.
Gandolfi et al., *J. Theor. Biol.*, vol. 92, pp. 57–84; 1981.
Devey et al., *Elisa and Other Solid Phase Immunoussays*, Chapter 6, pp. 136–152; 1988.
Sciutto et al., *Molecular Immunology*, vol. 24, No. 6, pp. 577–585; 1987.
Steengaard et al., *Molecular Immunology*, vol. 17, pp. 689–698; 1980.
Roitt et al., *Immunology*, 1985.
Chemical Abstracts, vol. 109 No. 1, Abst. 4921t, p. 4926; 1988.

(List continued on next page.)

*Primary Examiner*—Frank C. Eisenschenk
*Attorney, Agent, or Firm*—Darby & Darby

[57] ABSTRACT

An isolated human natural IgM antibody immunoreactive with an epitope present on HIV-1 Tat protein is provided. Additionally, a method for the prognosis or diagnosis of AIDS in an individual infected with HIV including the steps of:

obtaining a body fluid from the individual, detecting or measuring natural human IgM antibodies in the body fluid of the individual and determining a Δ20–Δ2 value, and comparing the Δ20–Δ2 value obtained from the individual with a Δ20–Δ2 value obtained from clinically normal, non-HIV infected humans, wherein the individual has AIDS or will progress to AIDS within about two years if the individual's Δ20–Δ2 value is significantly decreased relative to the Δ20–Δ2 value obtained from the clinically normal humans, is provided.

1 Claim, 10 Drawing Sheets

OTHER PUBLICATIONS

Chemical Abstracts, vol. 107 No. 15, Abst. 132233r, p. 550; 1987.
Rodman et al., *Journal of Immunological Methods,* vol. 94, pp. 105–111, 1986.
Rodman et al., *Science,* vol. 258 No. 4704, pp. 1211–1215; Jun. 1985.
Jerne, *Proc. N.S.A.,* pp. 849–857; 1955.
Benner et al., *Immunology Today,* pp. 243–249; 1982.
Chow et al., *Int. J. Cancer,* vol. 27, pp. 459–469; 1981.
Wang et al., *San Diego Regional Cancer Center,* pp. 1–7; 1992.
Rodman, *Int'l. Conference on Advances in Aids Vaccine Development,* pp. 2–4; 1991.
Muller, *The Journal of Immunology,* vol. 147, pp. 933–941; 1991.
Hoffmann et al., *Proc. Natl. Acad. Sci. USA,* vol. 88, pp. 3060–3064; Apr. 1991.
Stein et al., *Clin. exp. Immunol.,* vol. 85, pp. 418–423; 1991.
DeFranco, *Nature,* vol. 357, pp. 14–15; 1992.
Sanchez, *Archives of Disease in Childhood,* pp. 657–661.
Rodman et al., *Clinical Immunology and Immunopathology,* vol. 57, pp. 430–440; 1990.
Rodman et al., *J. Exp. Med.,* vol. 175, pp. 1247–1253; 1992.
Berek et al., *Immunological Reviews,* No. 105, pp. 5–26; 1988.
Stollar, *Molecular Immunology,* vol. 28 No. 12, pp. 1399–1412; 1991.
Sanz et al., *The Journal of Immunology,* vol. 142 No. 11, pp. 4054–4061; 1989.
Hayakawa et al., *Proc. Natl. Acad. Sci. USA,* vol. 81, pp. 2494–2498; Apr. 1984,
Casali et al., *Immunology Today,* vol. 10 No. 11, pp. 364–368; 1987.
Lymberi et al., *Eur J. Immunol.,* pp. 702–707; 1985.
Rodman et al., *Science,* vol. 228, pp. 1211–1215, Jun. 1985.
Masson et al., *Clinica Chimica Acta,* pp. 735–730, 1966.
Goodman et al., *Journal of Reproductive Immunology,* vol. 3, pp. 99–108; 1981.
Hekman et al., *Protides of the Biological Fluids,* pp. 549–552; 1968.
Friesen, et al., *Journal of Applied Biochemistry 3,* pp. 164–175; 1981.
Metz–Boutigue et al., *Eur. J. Biochem,* pp. 659–676; 1984.
Anderson et al., *J. Mol. Biol.,* vol. 209, pp. 711–734; 1989.
Saint–Marc et al., *The Lancet,* vol. 340, pp. 1347; Nov. 1992.
Xu et al., *Disease Markers,* vol. 10, pp. 115–141; 1992.
Dietrich et al., *Clinical Immunology and Immunopathology,* vol. 62 No. 1, pp. S73–S81, 1992.
Dwyer, *The New England Journal of Medicine,* vol. 326 No. 2, pp. 107–116; 1992.
Hague, *Pediatrics,* vol. 89 No. 4, pp. 806–807, Apr. 1992.
Tatum, *Journal of Immunological Methods,* vol. 158, pp. 1–4, 1993.
Wordell, *Innovations in Antiviral Development and the Detection of Virus Infection,* pp. 173–183, 1992.
Kanakoudi–Tsakalidou, *J. Pediatrics,* vol. 119, pp. 624–629, 1991.
Towbin et al., *Proc. Natl. Acad. Sci. USA,* vol. 76 No. 9, pp. 4350–4354; Sep. 1979.
Munoz et al., *Journal of Immunological Methods,* pp, 137–144; 1986.
Paul (ed.), *Immunology,* Raven Press, pp. 612–614, 1984.
Hirohata et al., *Journal of the Neurological Sciences,* pp. 115–118; 1985.
Butler et al., *Federation Proceedings,* vol. 46 No. 8, pp. 2548–2556.
Collins, *Alternative Immunoassays,* John Wiley & Sons, pp. 78–86; 1984.

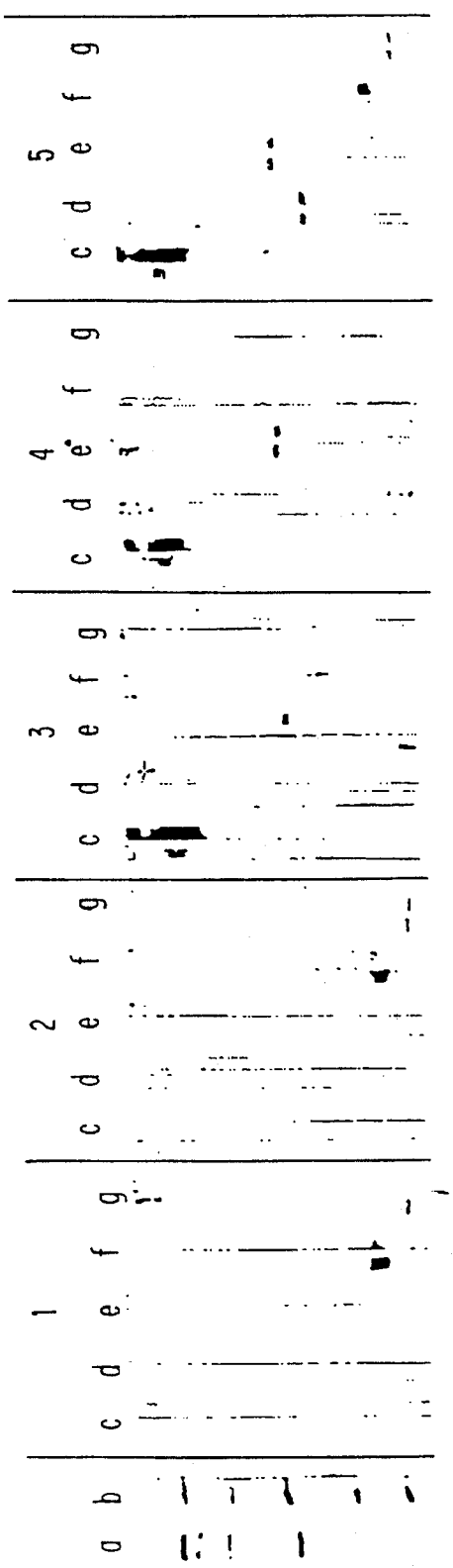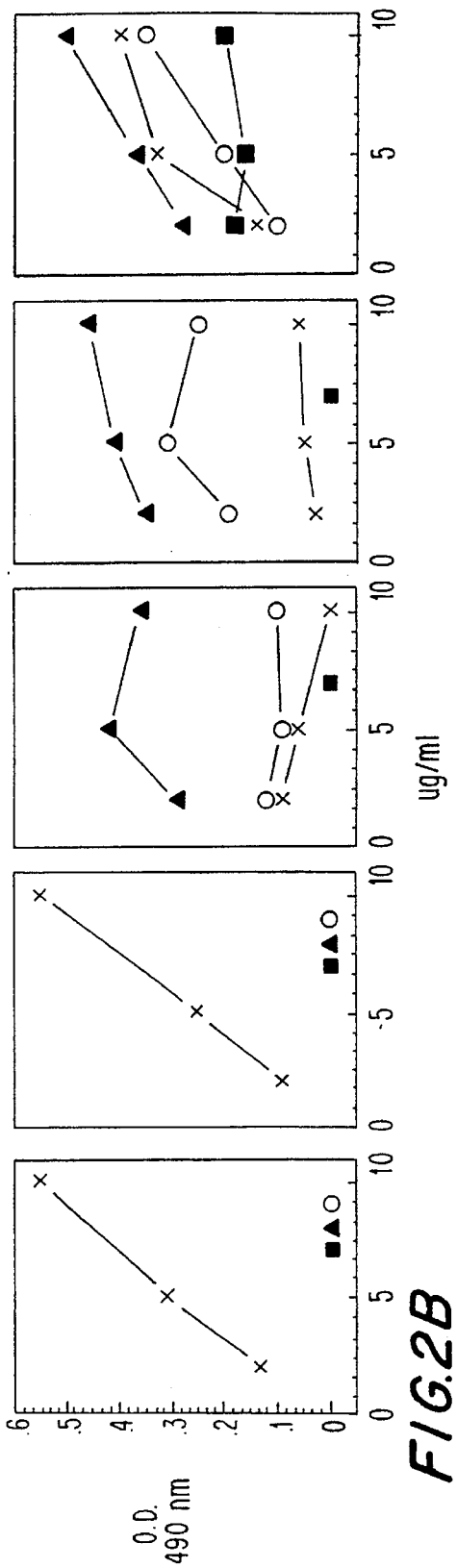
FIG.2A
FIG.2B

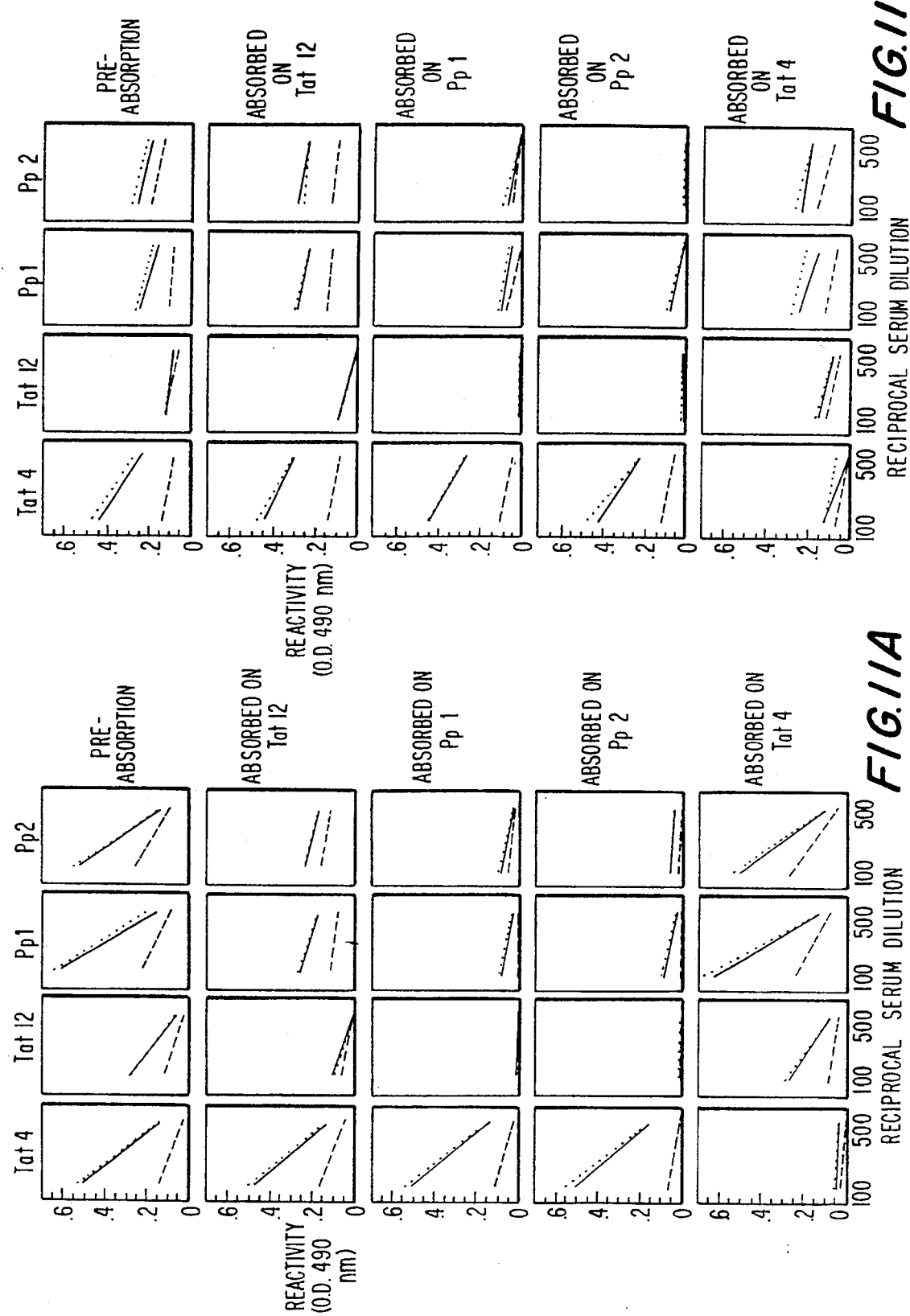

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Human immunodeficiency virus type 1

( v i i ) IMMEDIATE SOURCE:
        ( B ) CLONE: tat #1

( x i ) SEQUENCE DESCRIPTION: SEQ ID NO:1:

Met Glu Pro Val Asp Pro Arg Leu Glu Pro Trp Lys
    1                 5                         10

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

( v i i ) IMMEDIATE SOURCE:
        ( B ) CLONE: tat #2

( x i ) SEQUENCE DESCRIPTION: SEQ ID NO:2:

Leu Glu Pro Trp Lys His Pro Gly Ser Gln Pro Lys
    1                 5                         10

( 2 ) INFORMATION FOR SEQ ID NO:3:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Human immunodeficiency virus type 1

( v i i ) IMMEDIATE SOURCE:
    ( B ) CLONE: tat #3

( x i ) SEQUENCE DESCRIPTION: SEQ ID NO:3:

Gly Ser Gln Pro Lys Thr Ala Cys Thr Asn Cys Thr
1               5                   10

( 2 ) INFORMATION FOR SEQ ID NO:4:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Human immunodeficiency virus type 1

( v i i ) IMMEDIATE SOURCE:
    ( B ) CLONE: tat #4

( x i ) SEQUENCE DESCRIPTION: SEQ ID NO:4:

Cys Thr Asn Cys Tyr Cys Lys Lys Cys Cys Phe His
1               5                   10

( 2 ) INFORMATION FOR SEQ ID NO:5:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Human immunodeficiency virus type 1

( v i i ) IMMEDIATE SOURCE:
    ( B ) CLONE: tat #5

( x i ) SEQUENCE DESCRIPTION: SEQ ID NO:5:

Lys Cys Cys Phe His Cys Gln Val Cys Phe Ile Thr
1               5                   10

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

( v i i ) IMMEDIATE SOURCE:
        ( B ) CLONE: tat #6

( x i ) SEQUENCE DESCRIPTION: SEQ ID NO:6:

```
Val Cys Phe Ile Thr Lys Ala Leu Gly Ile Ser Thr
 1               5                   10
```

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

( v i i ) IMMEDIATE SOURCE:
        ( B ) CLONE: tat #7

( x i ) SEQUENCE DESCRIPTION: SEQ ID NO:7:

```
Leu Gly Ile Ser Tyr Gly Arg Lys Lys Arg Arg Gln
 1               5                   10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

( v i i ) IMMEDIATE SOURCE:
        ( B ) CLONE: tat #8

( x i ) SEQUENCE DESCRIPTION: SEQ ID NO:8:

Lys Lys Arg Arg Gln Arg Arg Arg Pro Pro Gln Gly
 1               5                   10

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

( v i i ) IMMEDIATE SOURCE:
        ( B ) CLONE: tat #9

( x i ) SEQUENCE DESCRIPTION: SEQ ID NO:9:

Arg Pro Pro Gln Gly Ser Gln Thr His Gln Val Ser
 1               5                   10

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

( v i i ) IMMEDIATE SOURCE:
        ( B ) CLONE: tar #10

( x i ) SEQUENCE DESCRIPTION: SEQ ID NO:10:

Thr His Gln Val Ser Leu Ser Lys Gln Pro Thr Ser
 1               5                   10

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Human immunodeficiency virus type 1

(v i i) IMMEDIATE SOURCE:
    (B) CLONE: tat #11

(x i) SEQUENCE DESCRIPTION: SEQ ID NO:11:

Lys Gln Pro Thr Ser Gln Ser Arg Gly Asp Pro Thr
1               5                   10

(2) INFORMATION FOR SEQ ID NO:12:

(i) SEQUENCE CHARACTERISTICS:
       (A) LENGTH: 12 amino acids
       (B) TYPE: amino acid
       (C) STRANDEDNESS: single
       (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
       (A) ORGANISM: Human immunodeficiency virus type 1

(v i i) IMMEDIATE SOURCE:
       (B) CLONE: tat #12

(x i) SEQUENCE DESCRIPTION: SEQ ID NO:12:

Gly Arg Lys Lys Arg Arg Gln Arg Arg Pro Pro
1               5                   10

(2) INFORMATION FOR SEQ ID NO:13:

(i) SEQUENCE CHARACTERISTICS:
       (A) LENGTH: 12 amino acids
       (B) TYPE: amino acid
       (C) STRANDEDNESS: single
       (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
       (A) ORGANISM: Human immunodeficiency virus type 1

(v i i) IMMEDIATE SOURCE:
       (B) CLONE: pp #1

(x i) SEQUENCE DESCRIPTION: SEQ ID NO:13:

Ser Cys Arg His Arg Arg Arg His Arg Arg Gly Cys
1               5                   10

(2) INFORMATION FOR SEQ ID NO:14:

(i) SEQUENCE CHARACTERISTICS:
       (A) LENGTH: 12 amino acids
       (B) TYPE: amino acid
       (C) STRANDEDNESS: single
       (D) TOPOLOGY: linear (i i) MOLECULE TYPE: peptide (i i i) HYPOTHETICAL: NO (i v) ANTI-SENSE: NO (v) FRAGMENT TYPE: internal (vi) ORIGINAL SOURCE:
    (A) ORGANISM: Human immunodeficiency virus type 1

(vii) IMMEDIATE SOURCE:
    (B) CLONE: pp #2

(xi) SEQUENCE DESCRIPTION: SEQ ID NO:14:

```
Arg Cys Cys Arg Arg Arg Lys Arg Arg Ser Cys Arg
 1               5                  10
```

(2) INFORMATION FOR SEQ ID NO:15:

(i) SEQUENCE CHARACTERISTICS:
        (A) LENGTH: 82
        (B) TYPE: amino acid
        (C) STRANDEDNESS: single
        (D) TOPOLOGY: linear (ii) SEQUENCE DESCRIPTION: SEQ ID NO:15:

```
Met Glu Pro Val Asp Pro Arg Leu Glu Pro Trp Lys His Pro Gly
 1               5                  10                  15

Ser Gln Pro Lys Thr Ala Cys Thr Asn Cys Tyr Cys Lys Lys Cys
                20                  25                  30

Cys Phe His Cys Gln Val Cys Phe Ile Thr Lys Ala Leu Gly Ile
                35                  40                  45

Ser Tyr Gly Arg Lys Lys Arg Arg Gln Arg Arg Pro Pro Gln
                50                  55                  60

Glu Ser Gln Thr His Gln Val Ser Leu Ser Lys Gln Pro Thr Ser
                65                  70                  75

Gln Ser Arg Gly Asp Pro Thr
                80
```

NATURAL HUMAN IGM ANTIBODIES IMMUNOREACTIVE WITH THE TAT PROTEIN OF HIV-1

This application is a continuation-in-part of:

U.S. patent application Ser. No. 07/173,705, filed Mar. 25, 1988 (abandoned);

U.S. patent application Ser. No. 07/873,917, filed Apr. 24, 1992 (abandoned);

U.S. patent application Ser. No. 07/912,026, filed Jul. 9, 1992 (abandoned); and U.S. patent application Ser. No. 07/924,412, filed Jul. 30, 1992 (abandoned).

FIELD OF THE INVENTION

The present invention relates to natural human IgM antibodies, and their uses in prognosis, diagnosis, and therapy. In particular, the invention relates to natural human serum IgM antibodies which can recognize epitopes present on human protamine, HIV Tat protein and SP80, a seminal plasma homologue of human lactoferrin, and which, in accord with historic characterization of natural antibodies, exhibit low binding affinity to antigen. This low affinity antibody subset of serum IgM antibodies may be assayed for prognosis or diagnosis and administered for treatment of AIDS. Methods for the detection and/or measurement, isolation and use of the low affinity natural human serum IgM antibodies are provided.

BACKGROUND OF THE INVENTION

The natural antibody repertoire is a segment of the immune system that is little understood, was early postulated to provide a first defense against specific infectious agents (Michael, J. G., 1969, *Curr. Top. Microbiol. Immunol.* 48:43–62), and has recently been the subject of increased interest and conjecture of a possible role in control of autoimmunity (Cohen, I. et al., 1986, *Immunol. Today* 2:363–364) or other phases of immunoregulation (Dighiero, G. et al., 1985, *J. Immunol.* 134:765). Natural antibodies frequently have been designated as those of lower affinity than their induced counterparts (see, e.g., Day, E. D. et al., *J. Neuroimmunol.* 13:143–158, 1986; Hoch, S. et al., *J. Immunol.* 136:892–897, 1986; Tongio, M. M. et al., *Tissue Antigens* 26:27–285, 1985).

Natural antibodies, in accordance with the long held and recently fortified hypothesis that the humoral immune system includes a repertoire of "natural" (Jerne, N. K., *Proc. Natl. Acad. Sci. USA* 41: 849, 1955) or "naive" (Berek, G. et al., *Immunol. Rev.* 105: 5–26, 1988) antibodies, not attributable to immune induction, are the subject of much speculation. The various characteristics attributed to that class of antibodies include: germ line configuration of VH and VL segments (Stollar, D. *Mol. Immunol.*, 28:1339, 1991; Sanz, I. et al., *J. Immunol.* 142:4054, 1989), IgM of low affinity (Rodman, T. C. et al., *Clin. Immunol. Immunopath.* 57:430, 1990), secretion by CD5$^+$B-cells (Hayakawa, K. et al., *Proc. Natl. Acad. Sci. USA* 81:2494, 1984), polyreactivity (Casali, P. et al., *Immunol. Today* 10:364, 1989; Lymberi, P. et al., *Eur. J. Immunol.* 57:702, 1985) and presence in sera of all normal individuals with apparent quiescence until needed to provide "first line of defense" (Lymbori, P. et al., supra) against new infectious invaders.

Natural antibodies constitute a repertoire, usually IgM, occurring in sera of healthy children and adults, with no basis for assignment of antigen mediated induction (Jerne, N. K., Supra 41:849, 1955; Michael, J. G. et al., *J. Exp. Med.* 118:619, 1963; J. Boyden, S. V., *Adv. Immunol.* 5:1, 1966; Denis, K. A. et al., *J. Exp. Med.* 157:1170, 1983; Rodman, T. C. et al., *Science* 228:1211, 1985; Berek, C. et al., supra; Coutinho, A. et al., *Cold Spring Harbor Symp. Quant. Biol.* 54:159, 1990; Avrameas, S., *Immunol. Today* 12: 154, 1991). Natural antibodies have been frequently characterized as polyspecific (Guilbert, B. et al., *J. Immunol.* 128:2779, 1982; Martini, T. et al., *J. Exp. Med.* 175:983, 1992). Recent studies (Stollar, B. D., *Mol. Immunol.* 28: 1399, 1990; Valera, F. et al., *Proc. Natl Acad. Sci. USA* 88:5917, 1991; Algiman, M. et al., *Proc. Natl. Acad. Sci. USA* 89:3795, 1992; Kasaian, M. T. et al., *J. Immunol.* 148:2690, 1992; Rodman, T. C. et al., *J. Exp. Med.* 167:1228, 1988; Rodman, T. C. et al., *Clin. Immunol. Immunopath.* 57:430, 1990; Rodman, T. C. et al., *Abstr. PoA* 2429, VIII Internatl. Conf. AIDS, 1992; T. C. Rodman et al. submitted) however, have demonstrated a high order of epitopic specificity for certain sets of natural antibodies. Although no specific role or participation in immune mechanisms has been defined for any set, the proposition that natural antibodies may provide a "first line of defense" (Casali, P. et al., *Ann Rev. Immunol.* 7:513, 1989) against a new invader, while the forces of induced immune action are marshalled, is credible.

Acquired Immunodeficiency Syndrome (AIDS) is a disease which is characterized by a severe immune deficiency primarily caused by a decreased cell-mediated immune response (Gottlieb, M. et al., *N. Engl. J. Med.* 305:1425, 1981; Masur, J. et al., *N. Engl. J. Med.* 305:1431, 1981). The immunodeficiency state is characterized by a decrease in T helper lymphocytes (CD4$^+$ cells), a reversal of the normal CD4 (T4)+:CD8 (T8)+ cell ratio, lymphopenia, an increased incidence of opportunistic infections (e.g., *Pneumocystis carinii*), and/or malignancy (e.g., lymphoma or *Kaposis sarcoma*). The syndrome is usually fatal.

The causative agent of AIDS is a retrovirus, now termed Human Immunodeficiency Virus (HIV) (also known as LAV/ARV/HTLV III) which infects T helper lymphocytes (Gallo, R. C. et al., *Science* 224:500, 1984; Barre-Sinoussi, F. et al., *Science* 220:868, 1983; Feorino, P. M. et al., *Science* 225:69, 1984; Levy, J. A. et al., *Science* 225:840, 1984). The CD4$^+$ T-cell surface molecule has been identified as a receptor for the virus, and the virus' subsequent cytolytic activity depletes that cell population (Klatzman, D. et al., *Nature* 312:767, 1985; Dalgleish, A. G. et al., *Nature* 312:763, 1984; McDougal, J. S. et al., *Science* 231:382, 1986; Maddon, P. J. et al., *Cell* 47:333, 1986).

A patient is diagnosed with AIDS when he or she (1) tests positive for the presence of antibodies directed against HIV and presents with one or more of the specific indicator diseases (neoplasms, opportunistic infections) or (2) in the absence of laboratory evidence for HIV infection, all other causes of immunodeficiency are ruled out and one of the indicator diseases is present together with a low (less than 400/mm) CD4+ T lymphocyte count. AIDS-related complex (ARC) is a prodrome to AIDS and refers to those patients testing positive for HIV and presenting with persistent generalized lymphadenopathy, long-lasting fever, weight loss, persistent diarrhea, or extreme lassitude, but who have not yet developed one of the indicator diseases associated with full-blown AIDS.

U.S. patent application Ser. No. 07/924,412, discloses the presence of low affinity binding serum IgM antibodies immunoreactive with human protamines present in normal humans. These antibodies were detected upon observation of the curves of reactivity of IgM of normal, HIV negative sera with protamine (and peptides containing the immunoreactive epitope) at ascending antigen concentrations, wherein an increased rise in slope was found when assayed at higher antigen concentrations. The inference was made that the increase in rise of slope was a manifestation of the presence of a subset of antibodies with the same epitopic specificity as the principle subset, but of lower binding affinity. Review of the ontogenetic character of protamine led to the conclusion that the principle high affinity subset represented immunogenically induced antibodies and the low affinity subset were a set of natural antibodies. A formula was derived for measuring the difference in rise of slope of the curve for the 2 µg/ml antigen and that for the 20 µg/ml antigen: [(O.D. serum 1:100–O.D. serum 1:500) 20 µg/ml]–[(O.D. serum 1:100–O.D. serum 1:500) 2 µg/ml] or Δ20–Δ2, representing the proportionate titer of the low affinity binding IgM antibodies reactive with protamine. Calculation of Δ20–Δ2 for 60 HIV negative sera and 83 HIV positive sera showed that the values for 95% of the HIV positive sera were below the lower limit of the normal range, thus indicating that the low affinity subset of protamine reactive antibodies was selectively depleted in HIV positive sera, whereas the HIV positive (AIDS) serum, although displaying considerable protamine peptide reactivity, were more homogenous with respect to affinity. Therefore, it was concluded that a cohort of natural antibodies constituted a host factor of defense against HIV, maintaining a period of latency until, with failure of the immune system to develop an effective humoral arsenal against HIV and exhaustion of the pool of progenitors of natural antibodies, AIDS ensues.

SUMMARY OF THE INVENTION

The present invention relates to natural human IgM antibodies, and their uses in prognosis, diagnosis, and therapy of HIV infected individuals. In a specific embodiment, the invention relates to low affinity binding natural human serum IgM antibodies. In particular, such antibodies can recognize epitopes present on human protamines, HIV Tat protein and SP80, a seminal plasma homologue of human lactoferrin.

The low affinity subset of natural human IgM antibodies of the present invention may be assayed for prognosis or diagnosis of AIDS. Such antibodies are detectable in sera of normal subjects and HIV-infected individuals who subsequently exhibit a significant period of latency, but are absent or deficient in sera of individuals diagnosed with AIDS and sera of HIV infected individuals, who though asymptomatic at the time of the sampling, proceed to AIDS within a relatively short time. The invention provides methods for the detection and/or quantitative determination of the low affinity subset of serum IgM antibodies, for the prognosis and diagnosis of AIDS. In addition, such antibodies can be isolated from the CD5+ B-cells which produce them or from pooled serum and administered to patients diagnosed with AIDS and/or those patients where they are absent or deficient. Administration of these low affinity IgM antibodies is expected to restore the idiotypic network absent in these patients.

DEFINITIONS

As used herein, the following abbreviations and definitions will have the meanings indicated:

AIDS=acquired immunodeficiency syndrome
ARC=AIDS-related complex
BSA=bovine serum albumin
ELISA=enzyme-linked immunosorbent assay Fv=the variable region or antigen-combining site of an antibody molecule. This may be any fragment which contains the idiotype of the molecule including, but not limited to the Fab, F(abl) 21 Fabl, and the like.

HIV=Human Immunodeficiency Virus
P1=purified human protamine 1
P2=purified human protamine 2
Pp1=human Protamine 2b peptide amino acid residue nos. 33–44, SCRHRRRHRRGC.
Pp2=human Protamine 2b peptide amino acid residue no. 24–35, RCCRRRKRRSCR.
PAGE=polyacrylamide gel electrophoresis
PBS=phosphate-buffered saline "Proceeding to AIDS within a relatively short period of time" is defined herein as about less than 2 years.

BRIEF DESCRIPTION OF THE FIGURES

FIG. 2A—Immunotransfers of IgM and IgG reactivity of representative sera from the classes described in FIGS. 1A and 1B, with HIV structural proteins gp120, p24, the regulatory protein Nef, the recombinant Tat and a synthetic truncated Tat. Lane a, molecular weight markers on 10% polyacrylamide gel: 200 kD, 330 kD, 92 kD, 66 kD, 43 Kd; lane b, molecular weight markers on 12% gel; 92 kD, 615 kD, 43 kD, 30 kD, 20 kD, 14.4 kD. For each of the following lanes, the left hand member of the pair is IgM and the right hand member is IgG: lane c, gp120, 10% gel; lanes d–g 12% gel: lane d, p24; lane e, Nef; lane f, recombinant Tat; lane g, synthetic Tat (residues 1–68). Sera #1,2 are HIV-negative: sera #3,4 are from class 1, AIDS; serum #5 is from class 3, state-of-latency. The strong band at about 240 kD on the IgG member of lane c, sera 3,4,5 and the weak band at 45 kD for sera 3,5 were proven, by reactivity with a monoclonal antibody to gp 120, to be, respectively, a gp120 derived dimer and peptide (not shown).

FIG. 2B—ELISA of IgM reactivity of the same sera presented in FIG. 2A paralleling and supporting the inferenocs of the data for the reactions displayed in FIG. 2A. 1:100 dilution of each serum was assayed for IgM reactivity with 2 µg/ml, 5 µg/ml, 10 µg/ml of each protein and the corrected O.D. values plotted. The symbols represent: X Tat, A gp120, n p24, 0 Nef.

FIG. 5E—Fractions 1–8 of SP80 basic (lane b), SP80 acidic (lane c) and lectoferrin (LF) (lane d) obtained by cyanogen bromide (CNBr) cleavage. Glycan stained PAGE showing that SP80-acidic and LF are glycosylated, with the glycan moieties of each segregated in fraction 7, and that SP80-basic is not glycosylated.

FIG. 7B—Distribution of O.D. values (titers) obtained by ELISA of reactivity of human serum IgM with SP80, 1:100 dilution of serum with 20 µg/ml of SP80 fr7. HIV positive sera from patients classified at specimen collection as:

1. AIDS or ARC (n=20);
2. AIDS or ARC within 1 year (n=12);
3. variably symptomatic but not yet classified as AIDS or ARC within a year following specimen collection (n=24). With the lower limit of normal range of titers designated as O.D.=0.25, 4% of the HIV negative sera, 70% of group 1, 42% of group 2 and 13% of group 3 of the HIV positive sera show titers below normal.

Figure 8A:
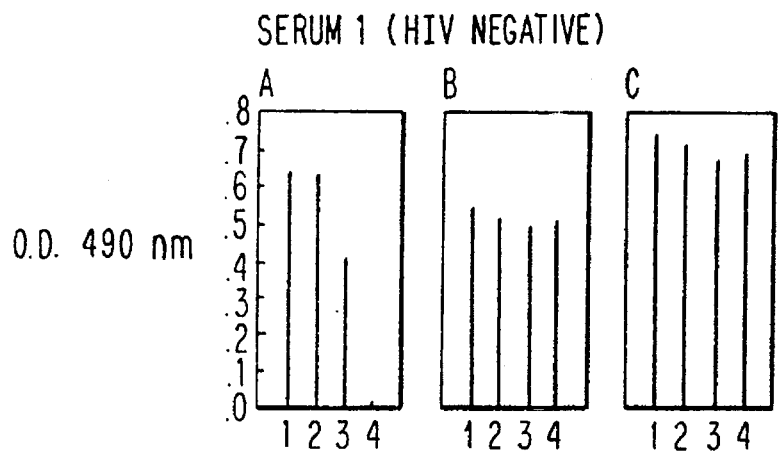

FIG. 8A—Residual reactivity of serum IgM with SP80 fr.7, following absorption on successively longer columns of resin complexed with SP80 fr7, showing specificity of antigen recognition of the natural IgM antibodies reactive with SP80 fr7.

1. unabsorbed serum;
2. serum passed through 6 mm column;
3. 21 mm column;
4. 35 mm column.

Figure 8B:
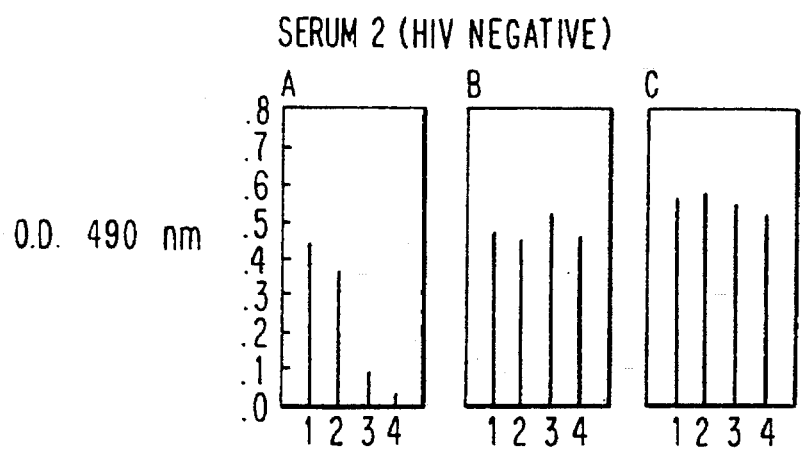

FIG. 8B—Residual reactivity of serum IgM with peptide 22–33 of HIV Tat, following absorption on successively longer columns of resin complexed with SP80 fr7, showing specificity of antigen recognition of the natural IgM antibodies reactive with SP80 fr7.

1. unabsorbed serum;
2. serum passed through 6 mm column;
3. 21 mm column;
4. 35 mm column.

Figure 8C:
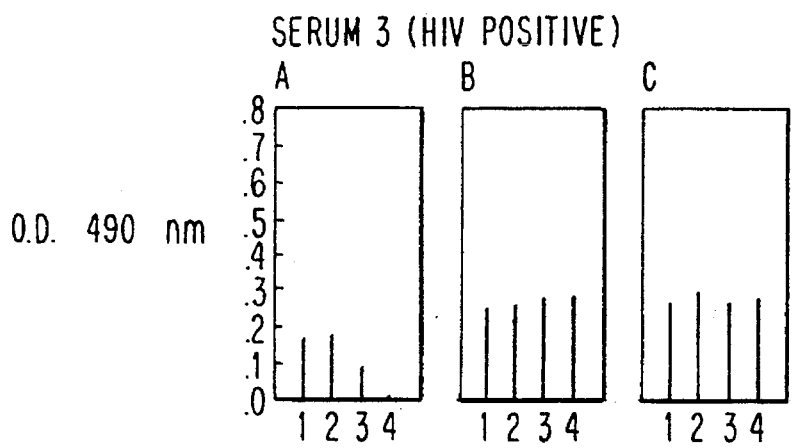

FIG. 8C—Residual reactivity of serum IgM with peptide 33–44 of human protamine 2b, following absorption on successively longer columns of resin complexed with SP80 fr7, showing specificity of antigen recognition of the natural IgM antibodies reactive with SP80 fr7.

1. unabsorbed serum;
2. serum passed through 6 mm column;
3. 21 mm column;
4. 35 mm column.

Progressively more SP80-reactive antibodies are absorbed out of the sera by passage through the three columns with complete depletion after passage through the 35 mm column, but no Tat peptide-reactive antibodies or protamine peptide-reactive antibodies are depleted by passage through any of the columns of SP80 fr7 complexed rosin.

Figure 9A:
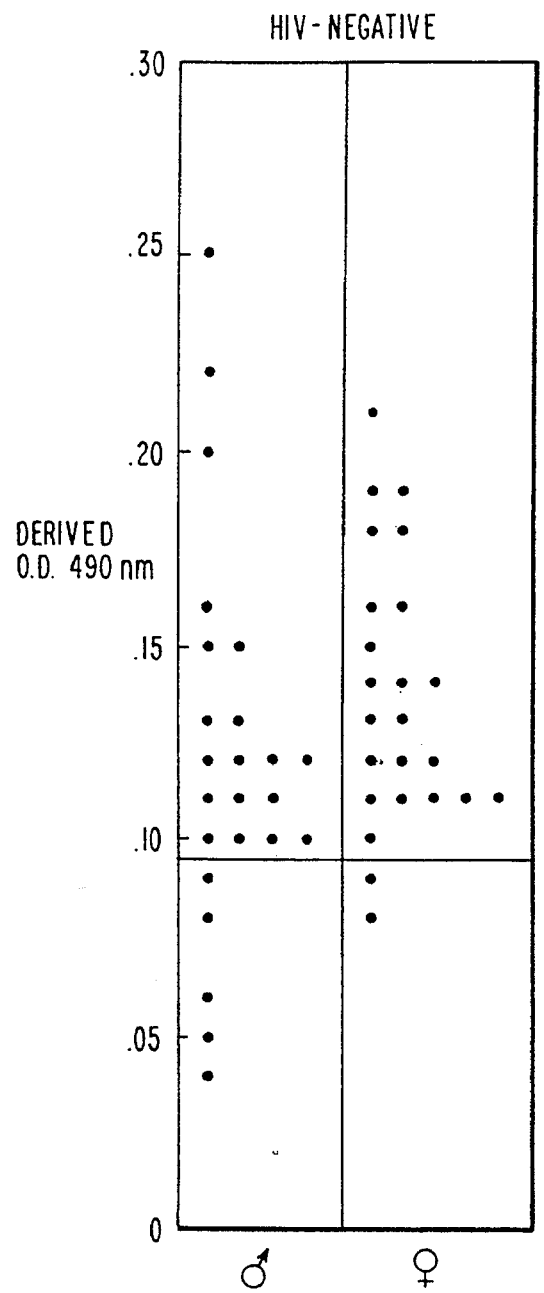

FIG. 9A—Distribution of derived O.D. values representing titers of low affinity IgM reactive with SP80. HIV negative sera from clinically normal males (n=24) and females (n=24).

Figure 9B:
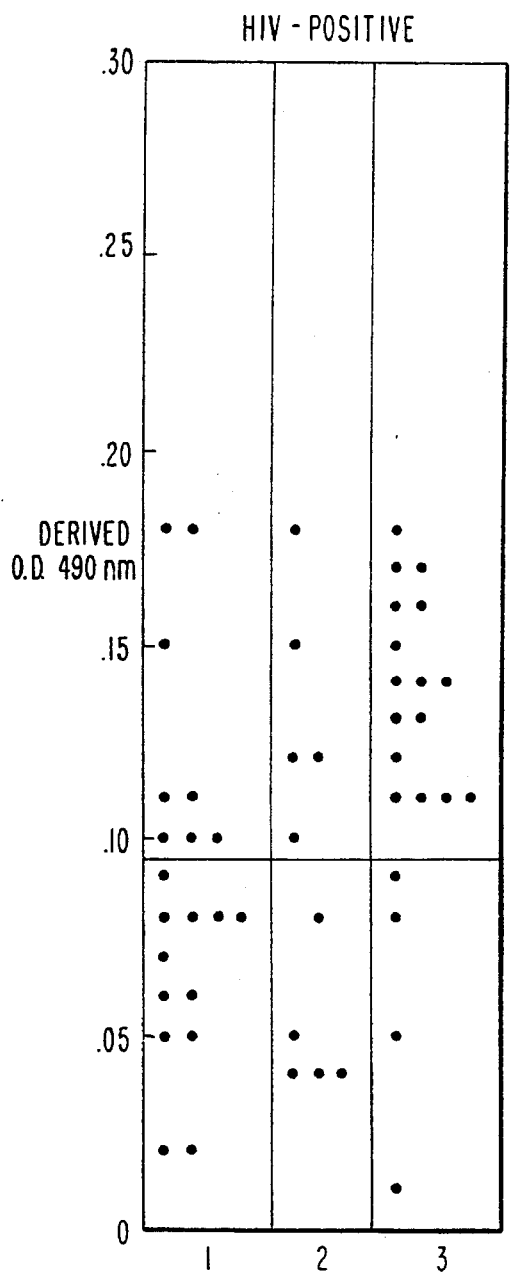

FIG. 9B—Distribution of derived O.D. values representing titers of low affinity IgM reactive with SP80. HIV positive sera from patients classified at specimen collection as:

1. AIDS or ARC(n=20)
2. AIDS or ARC within one year (n=10),
3. variably symptomatic, but not classified as AIDS or ARC within a year following specimen collection (n=20). 14% (7/48) of the HIV negative sera had values below 0.10, the arbitrarily designated lower limit of normal range; 60% (12/20) of class 1, 50% of class 2, and 20% (4/20) of class 3 had values below the limit.

Figure 10A:
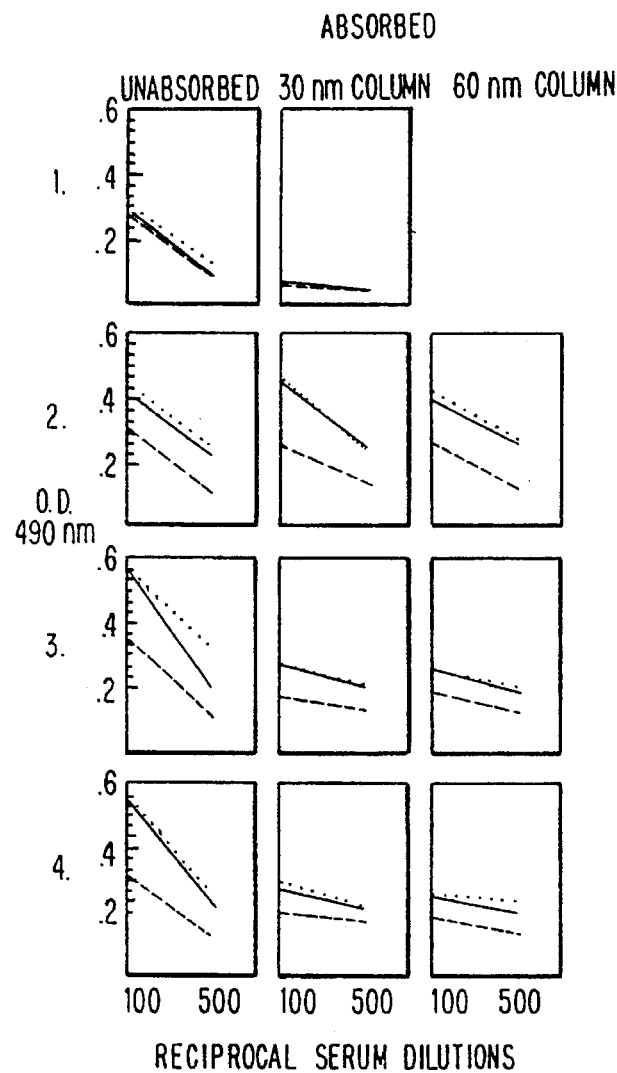

FIG. 10A—O.D. of reactivity with 1 Tat peptide 48–59, 2 Tat peptide 22–33, 3 Pp1, 4 Pp2. ELISA was carried out with serum dilutions 1:100 and 1:500 and peptide concentrations of - - - 2 µg/ml, ____ 10 µg/ml, . . . 20 µg/ml.

Figure 10B:
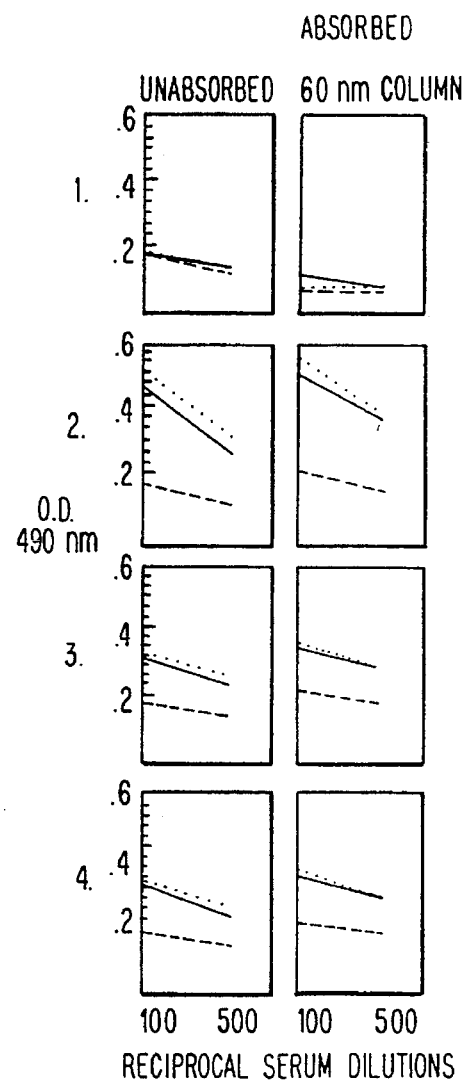

FIG. 10B—O.D. of reactivity with 1 Tat peptide 48–59, 2 Tat peptide 22–33, 3 Pp1, 4 Pp2. ELISA was carried out with serum dilutions 1:100 and 1:500 and peptide concentrations of - - - 2 µg/ml, ____ 10 µg/ml, . . . 20 µg/ml.

FIG. 11A—A series of graphs showing the depletion of protamine and Tat reactive IgM antibodies by passage over specific affinity columns.

FIG. 11B—A series of graphs showing the depletion of protamine and Tat-reactive IgM antibodies by passage over specific affinity columns.

DETAILED DESCRIPTION OF TEE INVENTION

All patents, patent applications and literature references cited in the specification are hereby incorporated by reference in their entirety. In the case of inconsistencies, the present disclosure, including definitions, will prevail.

The present invention is directed to natural human IgM antibodies, and their prognostic, diagnostic, and therapeutic uses. In particular, the invention relates to low-affinity binding, natural human serum IgM antibodies, which recognize three different epitopes: HIV Tat protein amino acid residue Nos. 22–33, HIV Tat protein amino acid residue Nos. 48–59 and SP80 a seminal plasma homologue of lactoferrin. The detection and/or measurement of any one of such subsets of antibodies in human sera can be used in diagnostic assays to predict the period of latency between HIV seropositivity and progression to clinical manifestations of AIDS. The invention also provides methods for treating HIV-infected individuals comprising administering these natural human IgM antibodies (including the total protamine-reactive, low affinity binding serum IgM natural antibodies disclosed in U.S. patent application Ser. No. 07/924,412) to such individuals.

As disclosed in copending U.S. patent application Ser. No. 07/924,412, it has been established that the sera of all clinically normal people over 12 days of age contain IgM antibodies reactive with protamines, that those antibodies are a definitive set of the circulating IgM with a high order of specificity, and the antigenic site with which those antibodies are reactive has been defined.

As described infra, the natural human IgM antibodies of the invention are detectable in significant titer in virtually all sera of normal adult males and females and of normal pediatrics (aged 7 days to 2 years). These human natural serum IgM antibodies are a discrete set with a high order of specificity.

The antibody molecules of the invention are IgM antibodies, including fragments thereof which contain the idiotypic region of the antibody molecules; these include but are not limited to the fragments which include the Fv region, such as the Fab, the F(ab'), Fab1 fragments and the like. Antibody fragments which contain the idiotype of the molecule could be generated by known techniques. For example, such fragments include but are not limited to: the F(ab1)2 fragment which can be produced by pepsin digestion of the antibody molecule; the Fab1 fragments which can be generated by reducing the disulfide bridges of the F(ab')2 fragment, and the Fab fragments which can be generated by treating the antibody molecule with papain and a reducing agent.

As shown below, human sera contain HIV Tat reactive IgM antibodies which constitute two distinct sets. The specific epitopes for those two sets, characterized as natural antibodies, have been identified as contained in peptides representing, respectively, residues 22–33, which has been shown to participate in Tat function and residues 48–59, the arginine rich region through which nuclear localization of Tat and its binding to viral RNA are mediated. Thus, the two sets of HIV Tat reactive natural antibodies of HIV negative and of HIV positive sera are coincident with the two regions of Tat, including specific residues, shown to be essential for its function in transactivation of HIV RNA and consequent replication of the virus. The implications are provocative. As noted, the proposed function of natural antibodies is that of provision of early defense (Casali, P. et al., *Ann Rev. Immunol.* 7:513, 1989). Thus far, there has been little basis for postulating the mechanism of that defense. The observations, presented herein, of the coincidence of reactive sites for two sets of natural antibodies with the function sites of an HIV regulatory protein may be relevant to that mechanism.

USE IN PROGNOSTICS AND DIAGNOSTICS: PREDICTION OF LATENCY FROM HIV INFECTION TO MANIFESTATION OF AIDS

As detailed below, the measurement of the natural human IgM antibodies of the present invention provides a reliable prognostic indicator of the period of latency between HIV infection and the onset of manifestations of AIDS. The presence or absence in serum of the natural human IgM antibodies of the invention is indicative of the capacity of an HIV-infected individual to withstand the pathogenetic progression to AIDS. The characteristic property of this subset of IgM antibodies (whose absence from serum correlates with a relatively short period of HIV latency) is the low binding affinity relative to other IgM antibodies present in adult sera. These low affinity IgM antibodies are reactive with epitopes present in HIV Tat protein and human SP80. Such low-affinity antibodies are believed to be natural antibodies.

The low affinity subset of serum human natural IgM antibodies may be assayed for prognosis of AIDS. Such antibodies are detectable in sera of normal subjects and HIV-infected individuals who subsequently exhibit a significant period of latency, but are absent or deficient in sera of individuals diagnosed with AIDS and sera of HIV infected individuals who, though asymptomatic at the time of the sampling, proceed to AIDS within a relatively short time (less than about 18 months). Thus, quantitative determination of the absence or deficiency of such antibodies in HIV-seropositive individuals can be relied on as an indication of relatively imminent onset of AIDS.

The quantitative determination and/or detection of low-affinity human natural serum IgM can also be used to monitor the efficacy of therapeutic treatments, to assist in selection of appropriate subjects for clinical trials, and to provide an additional modality for diagnosis of AIDS or ARC. It is also envisioned that the detection and/or measurement of these antibodies may be used similarly in the prognosis and diagnosis of other immune abnormalities.

The various assays and methods for detection and quantitative determination which can be used are described below.

ASSAYS OF SERUM HUMAN NATURAL IgM ANTIBODIES

In a particular embodiment of the invention in which the assay is for prognosis and diagnosis of AIDS, the presence of the human natural IgM serum antibodies of the present invention can be assayed by any of the methods described below. As one example, a low-affinity subpopulation of these IgM antibodies can be identified by allowing a fixed volume of the antibody mixture (e.g., serum) to react with increasing amount of antigen. As concentration of antigen increases, high affinity antibodies are saturated and antibodies of lower affinity will react with antigen. In a preferred embodiment, the ELISA described below can be used.

ASSAY SYSTEMS

Any assay system known in the art may be used for quantitative determination and/or detection of the natural human IgM antibodies (or antigen binding region thereof) of the invention. For example, such assays include but are not limited to the following immunoassays, including competitive and noncompetitive assay systems: radioimmunoassays, ELISA (enzyme linked immunosorbent assay), "sandwich"

immunoassays, precipitin reactions, gel diffusion precipitin reactions, immunodiffusion assays, agglutination assays, complement-fixation assays, immunoradiometric assays, fluorescent immunoassays, protein A immunoassays, and immunoelectrophoresis assays, to name but a few, as is well-known to those of ordinary skill in the art.

ASSAY METHOD FOR PREDICTION OF HIV LATENCY PERIOD

The assay and computation method described herein provides a modality for predicting the likely period of HIV latency before onset of AIDS, for an infected individual. Such information may be useful in the medical management of individual patients, in projection of community needs for medical care facilities, and in the selection of appropriate subjects for trial of proposed therapeutic agents. It also provides additional criteria for AIDS' diagnosis.

The assay and method described herein are but one example of the derivation of a quantitative index for use in AIDS' prognosis; other such examples, and modifications of the procedure herein described, are also envisioned and are within the scope of the invention. The assay described below makes use of low affinity protamine reactive antibodies as described in copending U.S. patent application Ser. No. 07/924,412. The same assay can be used for the detection and quantitation of the Tat- and SP80-reactive low affinity binding natural human antibodies described further below.

An enzyme-linked immunosorbent assay (ELISA) which can detect low-affinity binding, protamine-reactive serum IgM antibodies is described below. The ELISA is performed with ascending concentrations of antigen (e.g., protamine 2) at 2, 5, 10, 20, and 50 µg/ml. Briefly, the test procedure is comprised of the following steps:

(i) Antigen Coating

Assay wells of a microliter plate are coated with antigen (50 µl preferred), by addition of antigen solution to wells, followed by a 4 hour incubation. With protamine 2 as antigen, the preferred antigen concentrations for use are 2 µg/ml and 20 µg/ml.

(ii) Blocking

Antigen solution is washed out with buffer and all wells are filled to the brim with blocking solution (e.g. bovine serum albumin or BSA) to coat regions not coated with antigen, thereby inhibiting non-specific binding to the well surface in subsequent steps.

(iii) Binding of Serum Antibodies

Blocking solution is washed out and diluted serum (the same volume as the above antigen, 50 µl preferred) is added to each well. Each specimen serum is tested in triplicate at each of the two dilutions. Serum dilutions 1:100 and 1:500 are suitable when protamine 2 is used as antigen and, for most human sera, to have low enough serum background values for valid interpretation of test results to be made. However, with various peptides bearing the antigenic site, other pairs of serum dilutions varying from undiluted serum to 1:1000 dilution, are useful.

(iv) Detection If Bound IgM Antibodies

After 3 hours, serum dilutions are washed out and 50 µl peroxidase-labeled second antibody (anti-human IgM) is added to each well (the same preferred volume of the antigen or serum). After 1.5 hours, the second antibody is washed out, and 50 µl of peroxidase substrate is added. After 30 minutes, 50 µl of 2.5N sulfuric acid is added to each well to stop the action of enzyme (peroxidase) on substrate, thus terminating production of chromatic product.

(v) Measurement

The plate is placed in an automatic plate reader which moves the plate to center each well over a beam of filtered light so that the optical density (O.D.) of the incident light (e.g., 490 nm) is read for each well and recorded.

(vi) Computation

Optical density at 490 nm (O.D. 490) (Y axis) is then plotted against reciprocal serum dilution (X axis). An increase in slope of the reactivity curve at high antigen concentration is indicative of the presence of a secondary (low affinity) subset of natural human IgM antibodies. This increase is not seen in assays of sera from patients diagnosed with AIDS. Thus, the observed absence of the increase in slope of the reactivity curve at high antigen concentration, representative of a low affinity subset of natural human IgM antibodies, can provide an additional modality for diagnosis of AIDS or ARC.

A system of computation can be devised to quantitate this low affinity subset of natural human IgM antibodies, i.e., to assess the proportionate titer of the secondary subset of natural human IgM antibodies represented by the increase in slope of the reactivity curve with high antigen concentration, as follows: 2 and 20 µg/ml are empirically selected as suitable test antigen concentrations. The rise of the slope of the curve between two points on the X axis, serum dilutions 1:100 (×1) and 500 (×2), may be expressed as the difference between the O.D. values on the Y axis for those two points. The increase in rise from that of the 2 µg antigen curve to that of the 20 µg curve is (O.D.×1−O.D.×2) at 20 µg/ml antigen minus (O.D.×1−O.D.×2) at 2 µg/ml antigen, and may be noted as Δ20−Δ2.

Values for Δ20−Δ2 are then computed. A value of "15" can be considered to be the lower limit of the "normal" range for the protamine-reactive IgM antibodies. Values of $O.D._{490}=0.10$ for Tat-reactive and $O.D._{490}=0.25$ for SP80-reactive IgM antibodies can be considered to be the lower limit of the "normal" range.[1] A value within the normal range for an HIV-seropositive serum is predictive of a latency period of at least two years before the manifestation of AIDS, and probably longer, while a low Δ20−Δ2 value is predictive that progression to the disease is imminent.

[1] These values are applicable only for the assay carried out as described below. However, throughout this application, "Δ20−Δ2" will be used to designate this value irrespective of the antigen concentration employed.

It should be noted that it has been found that, while optimum results are always obtained when the ratio of the two concentrations of the antigen is 1:10, good results are also obtainable with other pairs of concentrations.

It should also be noted that various body fluids of a patient may be used as an assay sample, e.g., serum, plasma, with serum preferred for use.

Figure 1A:
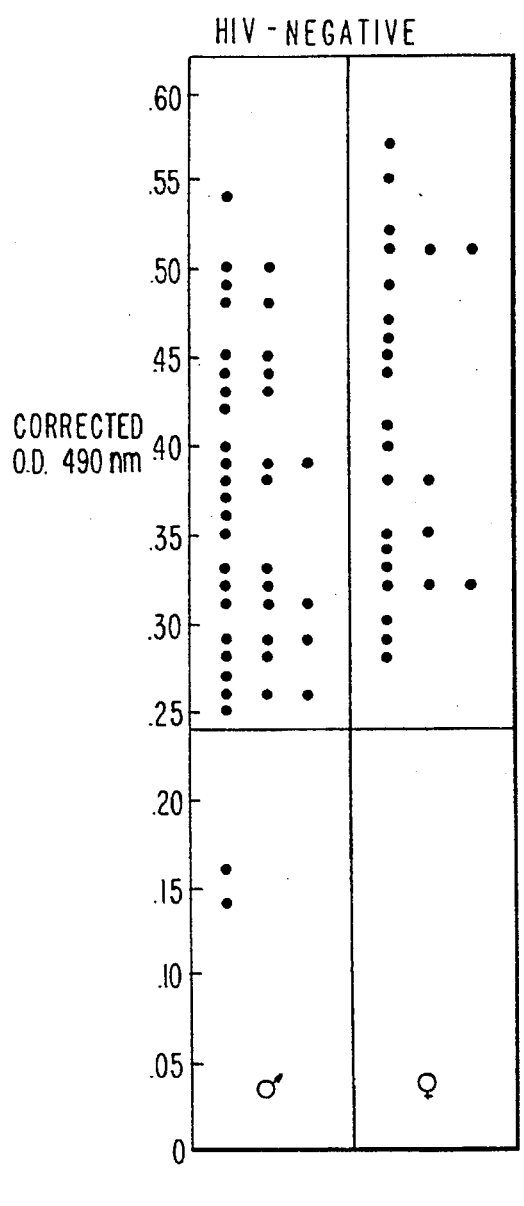
FIG. 1A—Titers, measured by ELISA and expressed as O.D. of IgM antibodies reactive with HIV Tat in sera of clinically normal, HIV negative males (n=41) and females (n=25).

The following is an explanation of the basis for derivation of the formula Δ20−Δ2 for expression of the proportionate titer of protamine-reactive IgM attributable to the low affinity subset. The data discussed below is from Rodman et al. (1990) *Clin. Immunol. Immunopathol.* 57, 430–440. The numerical values (O.D.) for the plotted points are as follows (taken from FIG. 1a, normal (HIV negative) serum at left):

| protamine µg/ml | 2 | 5 | 10 | 20 | 50 |
|---|---|---|---|---|---|
| serum 1:100 | 23 | 42 | 64 | 75 | 78 |
| serum 1:500 | 12 | 25 | 33 | 38 | 41 |
| (difference, = slope of the line between 100–500) | 11 | 17 | 31 | 37 | 37 |

At 2µg/ml the O.D. for serum 1:100 is 23 and for serum 1:500 it is 12. At 20 µg/ml the O.D. for 1:500 is 41. If no other antibody set reactive with antigen were present, the stoichiometrically expected O.D. for serum 1:100 (parallel with the 2 μg curve) would be 49 instead; it is 75. The difference between the values for 100 and 500 represent the slope of the line between those two measurements. (By formal definition, the slope of a line and the x-axis.) The difference between the expected parallel line and the actual line is the difference in slope (or, puristically, the rise in slope). That deviation from parallel indicates that reactivity in addition to that expected has been expressed and included in the measured O.D., i.e., that the reactivity of an additional set of antibodies reactive with that same antigen has been added onto the reactivity of the principle set. Considerable experimental evidence supports the conclusion that, in the ELISA, with antigen immobilized, the binding of antibodies with low binding affinity may not be detectable at low antigen concentration, but may be detectable at higher antigen concentration.

Thus, at 20 μg/ml the reactivity of the second antibody set, with lower binding affinity, is superimposed upon the reactivity of the principal set. Since the two sets have different binding constants the slopes of their lines between serum 1:500 and 1:100 are different and the slope of the composite line resulting from that superimposition is different from that expected if only the original (principal) set of antibodies were present. The rise in the slope of the line for the composite reactivities of the two sets represents that difference and may be expressed mathematically as: (O.D. serum 1:100–O.D. serum 1:500 at 20 μg) minus (O.D. serum 1:100–O.D. serum at 2μg) or Δ20–Δ2.

Thus, Δ20–Δ2 represents the increment in rise of the slope at 20 μg due to the superimposed reactivity of the low affinity set of antibodies. By that computation, the Δ20–Δ2 value of the example cited is 26, and that may be interpreted as the proportionate titer of the total reactivity of the serum IgM attributable to the low affinity subset.

The difference, at each antigen concentration, between the O.D. for serum 1:100 and serum 1:500, may be considered to represent the slope of that line. Thus, since the slope of the 5 μg line is greater than that of the 2 μg line, that of the 10 μg line is greater than that of the 5 μg line and that of the 20 μg line is greater than that of the 10 μg line, but that of the 50 μg line is not greater than that of the 20 μg line, the value for the slope of the 20 μg line may be considered to represent the maximum increment in reactivity due to the low affinity set. However, note: the selection of 2 and 20 is appropriate for this set of reactions; for quantitation of the proportionate titer of the natural antibody component of other systems, other sets of antigen concentrations may be appropriate and may be similarly determined.

Following the same rationale as that applied to the normal serum discussed above (FIG. 1a), the absence of the low affinity set of protamine-reactive antibodies in the AIDS serum (FIG. 3a, serum at left) is manifested by the absence of rise in slope at ascending antigen concentrations and a low (or zero) value for Δ20–Δ2.

| protamine μg/ml | 2 | 5 | 10 | 20 | 50 |
|---|---|---|---|---|---|
| serum 1:100 | 30 | 35 | 51 | 67 | 78 |
| serum 1:500 | 16 | 20 | 33 | 50 | 53 |
| (slope of the line between 100–500) | 14 | 15 | 18 | 17 | 15 |

Thus, although the total IgM reactivity with protamine of this AIDS serum is similar to that of the normal serum (described above) all of that reactivity may be attributed to a single antibody set reactive with antigen, i.e., the set immunogenically induced by protamine.

The rationale for immunogenic induction of protamine-reactive antibodies has been discussed (*Clin. Immunol. Immunopathol.* (1990) 57: 430) and may summarized by reminder of the ontogeny of protamine, a DNA binding protein unique to sperm that is synthesized de novo in the post-puberal testis within the immunologically privileged seminiferous tubules. Thus, protamine may be considered an immunologically non-self protein and induced antibodies to protamine may be expected to be present in post-puberal males and sexually experienced females.

The molecular basis for the difference in affinity for the two sets of protamine-reactive antibodies has not yet been resolved. The following possibilities are considered:

1. Although both subsets are reactive with the same decapeptide, the fine epitopic specificities may differ, e.g., at the level of position of a single amino acid residue.
2. As interest in natural antibodies and their possible relationship to development of autoantibodies has intensified, suggestions and indications of molecular characteristics unique to natural antibodies, e.g., in the CDR3 region (Chen, C., Stenzel-Poore, M. and Rittenberg, R., (1991) *J. Immunol.* 147, 2359–67) have been noted. It may be conjectured that such characteristics could be the basis for lower binding energy.

THERAPY

The natural human IgM antibodies of the invention may be used in therapy of AIDS and other immune abnormalities. It is envisioned that these antibodies may have a role in protecting an HIV-infected individual against the onset of AIDS. The antibodies may have similar protective effects in individuals afflicted with, or with a predisposition for, other conditions of immune abnormality. Thus, it is envisioned that the antibodies of the invention can confer short term protection to a host by passive immunotherapy, i.e., by the administration of such preformed low-affinity natural human IgM antibodies. Human immunoglobulin is preferred for such use because a heterologous immunoglobulin will provoke an immune response to its foreign immunogenic components. In one embodiment, the low affinity subset of natural human IgM antibodies of the invention may be isolated from pooled human sera in adequate quantities for use in passive immunotherapy, to defer the progression to AIDS in HIV positive individuals. The isolation of such human IgM antibodies is shown below in Example 5.

Alternatively, the CD5+ B-cells which produce the low affinity binding natural IgM antibodies of the present invention may be isolated. Such B-cells can be immortalized, cultured in vitro and the IgM antibodies produced therefrom isolated, using techniques well-known in the art. For example, once isolated, the CD5+ B-cells can be immortalized by, e.g., infection with Epstein Barr Virus (EBV) as disclosed in Casali, et al. (*Ann. Rev. Immunol.*, 7:513–535, 1989). The B-cells can also be cultured indefinitely after fusion with, for example heteromyeloma CB-F7 cells (Jahn, S., et al., *Clin. Exp. Immunol.*, 83:413–417, 1991). In any case, the low affinity IgM natural human antibodies of the present invention can be obtained from the supernatants of the immortalized B-cells or from the ascites fluid of mice inoculated with the immortalized B-cell and purified by techniques well-known in the art such as ammonium sulfate precipitation, affinity chromatography, HPLC, etc. Such isolated IgM antibodies can then be administered as described further below.

The natural human IgM antibodies of the present invention (including the anti-protamine IgM antibodies) can be used in a method for treating an individual infected with HIV comprising administering an amount of the natural antibodies effective for treating said individual.

Determining such effective amounts would require no more than routine procedures well known to those of ordinary skill in the art. For example, a relatively low dose, e.g. 0.1 mg/kg body weight could be administered per month and the patient closely monitored for any changed in $\Delta 20-\Delta 2$ value or disease status. If no effect is observed, incremental increases (e.g. log increases) of the natural human IgM antibodies of the present invention can be administered.

The preferred route of administration of the natural human IgM antibodies of the present invention is parenteral including intradermal, subcutaneous, intra-muscular, intra-peritoneal and preferably intravenous.

Any attenuation of the disease (e.g, prolongation of the latency period) pursuant to treatment with the natural human antibodies of the present invention is within the scope of the invention.

Molecular clones relating to the low affinity natural antibodies of the invention can be prepared by known techniques. Recombinant DNA methodology (as disclosed in Lerner, R. A. et al., *Science*, 258:1313–1314, 1992) may be used to construct nucleic acid sequences which encode a monoclonal antibody molecule or antigen binding region thereof, with properties similar to those of the low affinity natural human IgM antibodies of the present invention.

A murine monoclonal antibody molecule may also be valuable for use in passive immunotherapy, by construction of so-called "chimeric antibody" molecules. Chimeric antibody molecules may be prepared containing a mouse antigen-binding domain with human constant regions (Morrison et al., *Proc. Natl. Acad. Sci. USA* 81:6851, 1984; Takeda et al., *Nature* 314:452, 1985). Antibodies may be purified by known techniques, e.g., immunoabsorption or immunoaffinity chromatography, chromatographic methods such as HPLC (high performance liquid chromatography), or a combination thereof, etc.

The progression of HIV infection from state of latency to AIDS is accompanied by depletion of natural antibodies of the present invention. Thus, those natural antibodies may be a specific factor in maintenance of latency. For example, Tat protein is present in extracellular fluid of HIV infected cells in vitro and is believed to be present in circulating plasma of infected individuals (Ensoli, B. et al., *Nature* 345:84, 1990; Jacovits, A. et al., *Embo J.* 9:1165, 1990). Similarly, since Tat is endocytosed by T-cells and macrophages in vitro (Frankel, A. D. et al., *Cell* 55, 1988; Mann, D. A. et al., *EMBO J.* 10:1733, 1991), it is considered likely that the event occurs in vivo. Entry of Tat into resting non-productive HIV infected cells, therefore, may be an avenue through which an ever increasing number of cells is activated to produce virus, leading to the consequent pathogenetic progression to AIDS. A plasma borne host factor capable of suppressing Tat entry or function may indeed provide the means through which the unique and variable period of latency between HIV infection and AIDS is maintained. The continued presence of Tat may result in the progressive depletion of those antibodies. When their depletion is consummate their defense function may be abrogated and opportunistic infections enabled to flourish. Or, natural antibodies may be an integral part of an idiotypic network (e.g. ab 1) and perturbation of the network through depletion of ab 1 could result in autoimmunity or other disregulation of the immune system. Thus, perturbation of the network may be related—cause or effect—to the depletion of natural antibodies following HIV infection. That would be consonant with current interest in the possibility that an autoimmune factor may contribute to the pathogenetic progression from HIV infection to AIDS.

Two different HIV Tat-reactive natural human antibodies have now been discovered. As shown in the Examples below, the antibodies recognize HIV Tat amino acid residue Nos. 22–33 and 48–59. Both regions of Tat are essential for its function. Therefore, administration of these Tat-reactive IgM antibodies to HIV-infected individuals who have "lost" these antibodies and whose disease will progress to AIDS in less than two years is a particularly preferred embodiment of the present invention. It is envisioned that restoration of the natural human IgM antibodies disclosed herein to such patients will forestall their progression to full blown AIDS.

The natural antibodies of the present invention have also been detected in some commercial preparation of intravenous immunoglobulin (IVIG), although other commercial preparations of IVIG lack the natural IgM antibodies of the present invention. Such IVIG preparations are currently being successfully utilized to treat HIV-infected individuals (Saint-Marc, T., et al., *The Lancet,* 340:1347, 1992; Mofenson, L. M., et al., *JAMA,* 268:483–488, 1992). Therefore, it may be advantageous to test the commercial IVIG materials for the presence of the natural IgM antibodies of the present invention using the teachings presented herein as those that contain these antibodies are believed to be the most efficacious when administered to HIV-infected individuals. The data showing the presence of the natural IgM antibodies of the present invention in IVIG is presented below in Example 5.

Recently, Xu, H. et al. (*Disease Markers, Vol.* 10, 115–141, 1992) described a circulating low molecular weight IgM consisting of a monomeric subunit of the usual pentameric IgM molecule and its presence in autoimmune, infective, immunodeficient and B-cell disorder. Using an enhanced detection system, Xu, H. et al. (*J. Immunol. Meth.* 146: 241–247, 1992) were able to demonstrate the presence of low molecular weight, monomeric IgM in the sera of all normal adults analyzed and blood obtained from all newly delivered infants analyzed. Without wishing to be bound by theory, it is believed that the human natural IgM antibodies of the present invention are these monomeric, low molecular weight IgM antibodies described by Xu, H. et al. As the procedure of Xu, H. et al. (*J. Immunol. Meth.,* supra) was said to be a sensitive (being capable of detecting 2 pg/ml of monomeric IgM), quantitative reproducible method, this procedure can be employed to identify and use the human natural IgM antibodies of the present invention.

Pharmaceutical Formulations

The present invention also provides pharmaceutical formulations and dosage forms for parenteral use in treating an HIV infected individual to forestall the progression to AIDS. In general such dosage forms contain one or more of the natural human IgM antibodies according to the invention.

The pharmaceutical formulations of the present invention may include, as optional ingredients, pharmaceutically acceptable vehicles, carriers, diluents, solubilizing or emulsifying agents, and salts of the type that are well-known in the art. Nonlimiting examples of such substances include 0.5N saline, distilled water and 5% dextrose.

It will be appreciated that the unit content of active ingredient or ingredients contained in an individual oral or parenteral dose of each dosage form need not in itself constitute an effective amount since the necessary effective amount can be reached by administration of a plurality of dosage units.

The present invention is described further below in specific examples which are intended to further describe the invention without limiting its scope.

EXAMPLE 1: NATURAL HUMAN IgM ANTIBODIES ARE IMMUNOREACTIVE WITH HIV TAT PROTEIN AMINO ACID RESIDUE NOS. 22–33

MATERIALS AND METHODS

SERA

HIV-positive sera were collected from blood specimens of individuals at risk for AIDS during the period 1983–1990, and stored in small aliquots at −60° C. Diagnosis at specimen collection and at subsequent clinical examinations allowed the sera to be assigned to three classes: (1) AIDS, (2) AIDS within 1 year, and (3) asymptomatic or state of latency for >1 year. The HIV negative sera were selected randomly from a store of 200 specimens, including donations from laboratory personnel and discards from clinical laboratories identified by age, sex, and "no clinical findings." Those specimens also were collected throughout the period 1983–1990, and stored at 60° C. HIV positivity for all sera was determined by immunotransfer or by report from certified clinical laboratories.

ANTIGENS

Recombinant HIV Tat protein (complete, residues 1–86) representing the BH10, HxP2 isolates and HIV Nef expressed in *Escherichia coli*, HIV gp 120 and HIV p24 expressed in baculovirus, were obtained from American Biotechnologies Inc. (Cambridge, Mass.). Synthetic truncated Tat was a gift, prepared as described (Laurence, J. et al., *Proc. Nat. Acad. Sci. USA* 88:7635, 1991). 11 overlapping dodecapeptides of Tat, including residues 1–82, constructed from the sequence described (Frankel, A. D. et al., *Proc. Nat. Acad. Sci. USA* 86:7397, 1989), were prepared by Multiple Peptide Systems (San Diego, Calif.). Opp, a dodecapeptide representing residues 33–44 of human protamine 2b was prepared by the Rockefeller University Protein Sequencing Service. All peptides were synthesized by the method of Merrifield (Merrifield, R. B., *J. Am. Chem. Soc.* 85:2149, 1963), and amino acid content of each was varied by the Mass Spectrometric Biotechnology Resource of the Rockefeller University.

ELISA

IgM reactivity of each serum with Tat, peptides of Tat, gp120, p24 and Nef was determined by ELISA as described above. Briefly, 50 μl of 10 μg antigen/ml PBS was placed in each well (96-well microliter plates; Dynatech Laboratories, Inc., Alexandria, Va.), incubated at room temperature for 3 hours, blocked with 3% BSA overnight at 50° C., then with 1% preimmune rabbit serum for 1 hour. Blocking with preimmune rabbit serum eliminated background attributable to the second antibody. 50 μl of the test serum (1:100) was added to the wells, incubated for 2 hours, followed by 50 μl of the peroxidase-labeled second antibody: IgG isolated from serum of a rabbit immunized with purified total IgM from pooled normal sera, for 1.5 hours. 50 μl substrate, orthophenylene diamine (0.2 mg/ml) was added to each well, allowed to incubate for 30 minutes at room temperature, and the reaction stopped by the addition of 50 μl 12.5N $H_2SO_4$. After removal of each reagent, the wells were washed 20 times with 0.05% Tween 20/PBS. The O.D. at 490nm, of each well, was read in a microplate reader (MR 700; Dynatech Laboratories, Inc.). All appropriate controls were included and caveats for correction for background and other methodologic sources of error in the ELISA were observed (Pruslin, F. H. et al., *J. Immunol. Meth.* 137:27, 1991). Each plate included both HIV-positive and HIV-negative sera, each reaction was carried out in duplicate, and each serum was assayed two to five times. Throughout the study, a single normal serum was assayed for reactivity with HIV Tat 4–8 times with a mean corrected O.D. value of 0.50±1.2. ELISA with Pp as antigen and calculation of the proportionate titer of the low affinity subset of protamine-reactive IgM, designated as the natural antibody subset, was carried out as described above.

DITHIOTHREITOL (DTT) TREATMENT OF PEPTIDES

To determine whether the epitope of Tat with which the serum IgM antibodies are reactive is represented by the linear sequence of Tat peptide No. 4 (SEQ ID. NO:4) or by a conformation dependent structure resulting from S—S bonding of the cysteinyl residues, assay of the reactivity of HIV-negative and HIV-positive sera with Tat peptide No. 4 was carried out by the conventional procedure with the peptide in PBS and, in parallel, with Tat peptide No. 4 in 10 mm DTT/PBS. The same procedure was carried out for serum IgM reactivity with Pp (See Table 2).

IMMUNOTRANSFERS OF IgM AND IgG REACTIVITY

Immunotransfers of representative sera with each of the HIV proteins was carried out as follows. A wide PAGE of each HIV protein (gp120, p24,Nef, Tat, synthetic truncated Tat) was prepared and transferred to Immobilon P membrane. A pair of 2-mm strips, representing 1.5 μg protein each, were incubated in 1:100 dilution of serum for 2 hours at room temperature. The strips were washed with PBS/Tween 20, then one of each pair was incubated in peroxidase-labeled rabbit IgG anti-human IgM and the other in anti-human IgG, washed, and incubated in substrate, 3-amino-9-ethyl carbazole, for 1 hour. Reaction was stopped by washing ($H_2O$) and air drying.

RESULTS

ASSAY OF SERA FOR IgM REACTIVITY WITH TAT

Figure 1B:
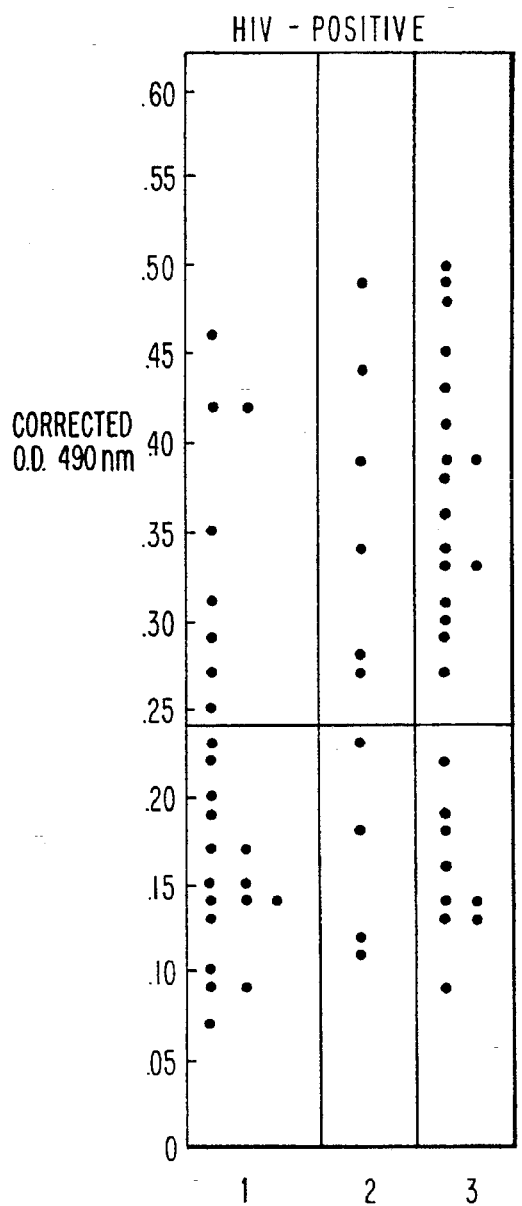
FIG. 1B—Titers, measured by ELISA and expressed as O.D. of IgM antibodies reactive with HIV Tat in sera of HIV-positive patients 1. diagnosed with AIDS at specimen collection (n=24),
2. diagnosed with AIDS within one year from specimen collection (n=10), and
3. asymptomatic or state-of-latency more than one year (n=26).

Sera of 66 HIV-negative and 60 HIV-positive adult males and females, none of whom had received antiviral or immune-corrective therapy, were assayed for IgM antibodies reactive with HIV Tat. As shown (FIG. 1A), of the HIV-negative sera from clinically normal subjects, 100% of the female and 95% of the male sera had titers within a circumscribed range. For the HIV-positive sera (FIG. 1B), 66% of those diagnosed with AIDS (Class 1), 40% of those from patients for whom a diagnosis of AIDS was entered within 1 year (Class 2), and 35 of those who remained AIDS free for >1 year (Class 3) had titers below that range. These data suggest that progression to AIDS is accompanied by a decline in HIV-positive sera of a constant component of normal sera: a set of IgM antibodies reactive with HIV Tat protein.

HIV-NEGATIVE SERA ARE NOT REACTIVE WITH HIV PROTEINS OTHER THAN TAT

Figure 3:
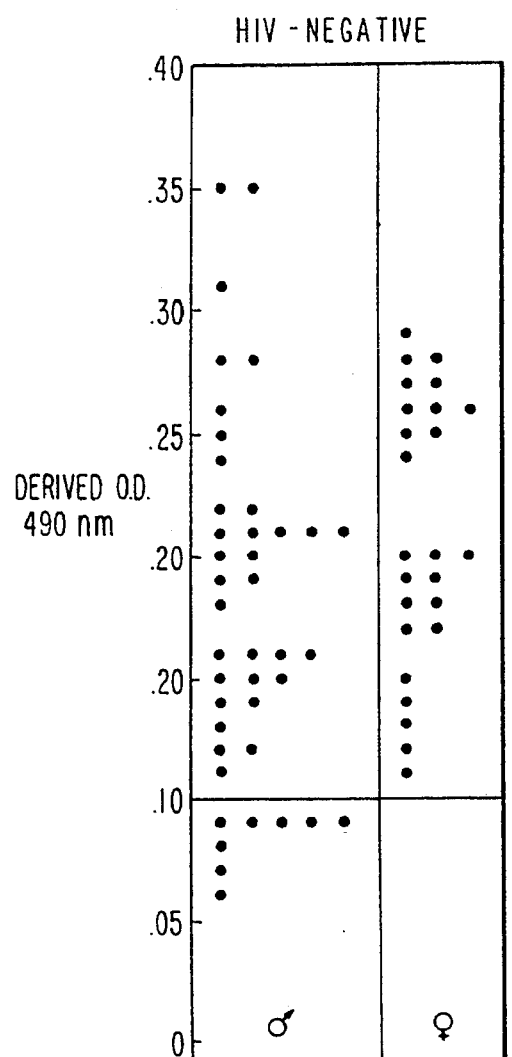
FIG. 3—Titers of the same sera as those of FIGS. 2A and 2B, measured by ELISA end expressed as the derived O.D. representing the subset of low affinity IgM antibodies, designated as natural antibodies reactive with pp, a peptide (residues 33–44) of human protamine 2b.

Further assurance for the specificity and unique occurrence of the Tat-reactive antibodies (FIGS. 2A and 2B) was sought by inspecting the reactivity of a representative group of sera with other HIV proteins as well as Tat, and by utilizing another method of immunochemical analysis (FIG. 3). The HIV proteins secreted for this comparison were the structural proteins gp120 and p24 and, in addition to Tat, another regulatory protein, Nef. The most frequently used criterion for HIV positivity is that of reactivity with the structural proteins. There is well-accepted evidence that antibodies to the envelope protein gp120 appear soon after infection and are present at all subsequently stages (Allan, J. et al., *Science* 228:1091, 1985), while antibodies to the gag protein, p24, decline as disease progresses (Biggar, R. J. et al., *Brit. Med. J.* 291:997, 1985). The role of the Nef protein in HIV replication or expression in vitro has not been clearly defined (Cullen, B. R., *FASEB J.* 5:2361, 1991). Detection of antibodies to HIV Nef in sera of patients at all stages of HIV infection has been reported (for review, see Culman, B. et al., *J. Immunol.* 146:1560, 1991); that prevalence, however, has been questioned (for review, see Cheingsongo-Popov et al., *AIDS Res. Hum. Retrovir.* 6:1089, 1990).

Detection of Tat-reactive IgG antibodies in some HIV-positive sera has been reported and interpreted as evidence of immune response to the viral protein; no reactivity with Tat by IgG of HIV-negative sera was observed (Krone, J. A. et al., *J. Med. Virol.* 26:261, 1988; Reiss, P. et al., *J. Acq. Immuno. Def. Synd.* 4:165, 1991). However, to correlate the data disclosed herein with those previously published (Krone, J. A. et al., supra.; Reiss, P. et al., supra), immunotransfers of IgG reactivity of each serum with each HIV protein were included (FIG. 2A). As shown in FIG. 2A, the IgG reactivity of each serum with each of that panel of HIV proteins is in accord with the referred published data.

Sera nos. 1 and 2 (HIV negative) show no reactivity with gp120; sera nos. 3, 4, and 5 (HIV positive) show weak IgM and strong IgG reactivity with gp120. Only serum No. 5 (state of latency) displays reactivity, IgM and IgG, with p24. The three HIV-positive sera (nos. 3, 4, and 5) show IgG reactivity with Nef, and sera nos. 4 and 5 show IgM reactivity, as well. In accordance with the data of FIG. 1, the HIV-negative sera (nos. 1 and 2) show high IgM reactivity with Tat, while the two AIDS sera (nos. 3 and 4) show no discernible reactivity, and the HIV-positive, state of latency serum show moderate IgM reactivity with Tat. Each display of IgM reactivity with Tat is accompanied by display of IgG reactivity, although the relative densities of the IgM and IgG bands differ for the HIV-negative and HIV-positive sera. Reactivity with the truncated synthetic Tat (FIG. 2, lane g) is comparable, for each serum, with that with the recombinant Tat (lane f), thus assuring that the observed reactivity is not attributable to autogenous proteins of the bacterial vector. The IgM reactivities displayed for each serum by the ELISA (FIG. 2B) are markedly consistent with those detected by the immunotransfers (FIG. 2A).

ASSAY OF SERA FOR NATURAL IgM ANTIBODIES REACTIVE WITH PP

This probe for natural antibodies reactive with HIV Tat was suggested by the linear sequence of the epitope for the set of protamine-reactive IgM antibodies previously characterized in U.S. patent application Ser. No. 07/924,412. That epitope was identified as one with a concentration of four arginyl residues, consisting of a triplet plus one within a six-residue sequence.

Therefore, the identification of an arginine-rich sequence in HIV Tat (Arya, S. K. et al., *Science* 229:69, 1985) was provocative and suggested that the same set of natural antibodies might display reactivity with Tat.

In that regard, each of the sera assayed for Tat-reactive IgM antibodies (FIGS. 1A and 1B) was assayed also for titers of natural IgM antibodies reactive with a peptide, Pp (FIG. 3), representing a 12-residue sequence of protamine and including one copy of the deduced epitope.

Figure 4:
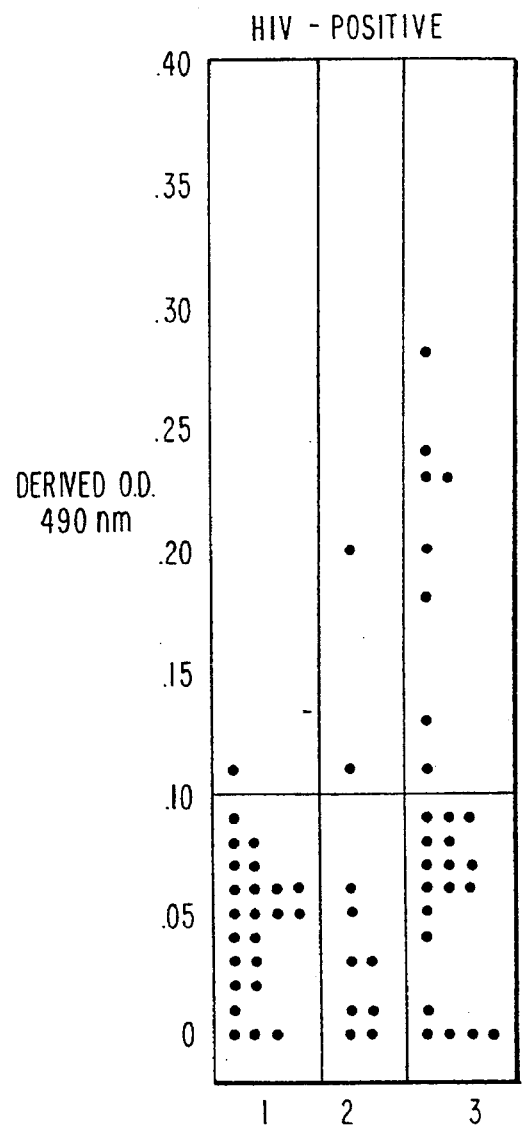
FIG. 4—With the lower limit of the normal range of titers designated as 0.10, 11% of the HIV-negative sera show titers below that limit. Of the HIV-positive sera, 96% of class 1 (AIDS), 80% of class 2 (AIDS within one year) and 71% of class 3 (state of latency) show titers below the designated lower limit of normal range.

The protocol and formula for deriving the proportionate titer of protamine-reactive IgM antibodies comprising the low affinity subset and designated as natural antibodies, distinct from a subset of high affinity IgM anti-bodies attributable to immunoinduction by protamine of sperm, have been described above. By application of that formula, the titer of natural antibodies reactive with Pp was derived for each serum (FIG. 3). As shown, the general distributions of Pp-reactive (FIG. 3) and Tat-reactive (FIGS. 1A and 1B) natural IgM antibodies in the various groups of sera are similar. With the lower limit of the normal range designated as 0.10, only 11% of the HIV-negative sera show titers of reactivity with Pp below that limit (FIG. 3A), while, of the HIV-positive sera (FIG. 4B), 96% of those from patients diagnosed with AIDS (class 1), 80% of those from patients diagnosed with AIDS within 1 year (class 2), and 71%. from those who remained AIDS-free for more than 1 year (class 3) show titers below the normal range.

PROBE FOR THE EPITOPE OF TAT RECOGNIZED BY SERUM IgM

Identification of the epitope was sought by assay of sera of each (as in one) of the two groups, HIV negative and HIV positive, for IgM reactivity against a series of overlapping peptides of Tat, Pp, and the total Tat. The results are set forth in Table 1 below.

TABLE 1

EPITOPE SPECIFICITY FOR HIV TAT-REACTIVE IgM ANTIBODIES

| | | | | O.D. 490 nm | | | | | |
| | | | | HIV-neg | | | HIV-pos | | |
| | Seq. ID. No. | Residues | Tat Peptides | Serum 1 | 2 | 3 | 4 | 5 | 6 |
|---|---|---|---|---|---|---|---|---|---|
| #1 | 1 | 1–12 | Met Glu Pro Val Asp Pro Arg Leu Glu Pro Trp Lys | — | — | — | — | — | — |
| #2 | 2 | 8–19 | Leu Glu Pro Trp Lys His Pro Gly Ser Gln Pro Lys | — | — | — | — | — | — |
| #3 | 3 | 15–26 | Gly Ser Gln Pro Lys Thr Ala Cys Thr Asn Cys Tyr | — | — | — | — | — | — |
| #4 | 4 | 22–33 | Cys Thr Asn Cys Tyr Cys Lys Lys Cys Cys Phe His | .26 | .31 | .13 | .11 | .21 | .21 |
| #5 | 5 | 29–40 | Lys Cys Cys Phe His Cys Gln Val Cys Phe Ile Thr | — | — | — | — | — | — |
| #6 | 6 | 36–47 | Val Cys Phe Ile Thr Lys Ala Leu Gly Ile Ser Tyr | — | — | — | — | — | — |
| #7 | 7 | 43–54 | Leu Gly Ile Ser Tyr Gly Arg Lys Lys Arg Arg Gln | — | — | — | — | — | — |
| #8 | 8 | 50–61 | Lys Lys Arg Arg Gln Arg Arg Pro Pro Gln Gly | — | — | — | — | — | — |
| #9 | 9 | 57–68 | Arg Pro Pro Gln Gly Ser Gln Thr His Gln Val Ser | — | — | — | — | — | — |
| #10 | 10 | 64–75 | Thr His Gln Val Ser Leu Ser Lys Gln Pro Thr Ser | — | — | — | — | — | — |
| #11 | 11 | 71–82 | Lys Gln Pro Thr Ser Gln Ser Arg Gly Asp Pro Thr | — | — | — | — | — | — |
| Pp1 | 13 | | Ser Cys Arg His Arg Arg Arg His Arg Arg Gly Cys | .24 | .39 | .22 | .26 | .18 | .20 |
| Tat | | (1–86) | | .35 | .49 | .33 | .09 | .17 | .20 |

The apparent homology of arginine distribution in Pp and Tat peptide No. 8 (SEQ ID NO:8) engendered the expectation that both would be recognized by the same set of IgM antibodies. It was particularly surprising, therefore, to observe no reactivity by any of the sera with the arginine-rich Tat peptide No. 8, nor with any of the Tat peptides other than peptide No. 4 (Table 1). All sera, of both groups, were reactive to varying degrees with Tat peptide No. 4, with Pp, and with total Tat. The limited homology between the two dodecapeptides, Tat peptide No. 4 and Pp, suggests that this study has revealed two sets of natural antibodies: one reactive with an epitope characteristic of Tat peptide No. 4, and another with an epitope indigenous to Pp, but not present in Tat peptide No. 4 nor in any linear sequence of Tat.

The assays of serum IgM reactivity with Tat and with the peptides of Tat displayed in Table 1 were carried out in the conventional protocol, which included solution of antigen in PBS. The presence of five cysteinyl residues in Tat peptide No. 4 suggested that the epitope might be dependent upon S—S bond-induced conformation. Therefore, HIV-negative and HIV-positive sera of each class were assayed for reactivity with Tat peptide No. 4 in 10 mm DTT and compared with the reactivity of peptide No. 4 in a conventional (nonreducing) medium. The sera were assayed also for comparative reactivity of Pp in conventional and reducing solution. The data are set forth in Table 2 below.

mational one that is recognized by both HIV-positive and HIV-negative sera.

EXAMPLE 2: NATURAL IgM ANTIBODIES REACTIVE WITH AN 80 kD SEMINAL PLASMA PROTEIN ARE PRESENT IN NORMAL AND DEFICIENT IN HIV-POSITIVE SERA

For each of the two sets of natural IgM antibodies defined above specific epitopic requirements were demonstrated suggesting that polyreactivity may not be an obligate property of natural (non-immune-induced) antibodies. That proposition is supported in the data presented below in which a third set of natural IgM antibodies displaying specific and selective epitope recognition, differing from that of the other two sets, are defined.

In the data presented in U.S. patent application Ser. No. 07/924,412 above, the dichotomy of "present in normal sera and absent or deficient in AIDS sera" for IgM antibodies reactive with a fraction of sperm surface components was demonstrated. The principle reactant of that fraction has now been identified as an 80 Kd protein (SP80) that is present in seminal plasma as both glycosylated and non-glycosylated variants, with adherence to sperm surface displayed only by the glycosylated form. The IgM natural antibody reactivity of SP80 has been resolved to a 10 Kd fragment of the

TABLE 2

A. HIV-1 Tat Protein

MEPVDPRLEPWKHPGSQPKTACTNCYCKKCCFHCQVCFITAKALGISYGRKKRRQRRRPPQGSQTHQVSLSKQPTSQSRGDPT

|  | Seq. ID No. | Residues | Sequence |
|---|---|---|---|
| Tat peptide | | | |
| 1 | 1 | 1–12 | MEPVDPRLEPWK |
| 2 | 2 | 8–19 | LEPWKHPGSQPK |
| 3 | 3 | 15–26 | GSQPKTACTNCY |
| 4 | 4 | 22–33 | CTNCYCKKCCFH |
| 5 | 5 | 29–40 | KCCFHCQVCFIT |
| 6 | 6 | 36–47 | VCFITKALGISY |
| 7 | 7 | 43–54 | LGISYGRKKRRQ |
| 8 | 8 | 50–51 | KKRRQRRRPPQG |
| 9 | 9 | 57–68 | RPPQGSQTHQVS |
| 10 | 10 | 64–75 | THQVSLSKQPTS |
| 11 | 11 | 71–82 | KQPTSQSRGDPT |
| 12 | 12 | 48–59 | GRKKRRQRRRPP |
| Protamine peptides | | | |
| Pp1 | 13 | 33–44 | SCRHRRRHRRGC |
| Pp2 | 14 | 24–35 | PSCRRRKRRSCR |

The data of Table 2 show that the reactivity of sera with Tat peptide No. 4 is virtually eliminated when the antigen is in the reduced state, thus establishing that the epitope on Tat peptide No. 4 is conformation dependent. With regard to Pp, the presence of DTT resulted in only moderate decline in reactivity, suggesting that the epitope of Pp recognized by serum IgM has little dependence upon the conformation induced by S—S bond between the two cysteinyl residues, and confirming the previous observations that the repetitive epitope of protamine is that of a triplet plus one of arginine in a linear six-residue piece. The demonstration of the difference in response to DTT treatment by the two peptides, Tat No. 4 and Pp, serves, fortuitously, to validate the discriminatory capability of that treatment for detecting S—S bond-dependent conformational epitopes and supports the interpretation that the epitope on HIV Tat is a confordenatured protein. Homology of SP80 with lactoferrin, an 80 kD iron-binding glycoprotein, found in milk, plasma, mucosal secretions and granules of neutrophilic leukocytes, has been reported or suggested (Masson, P. L. et al., *Clin. Chim. Acta* 14:735, 1966; Goodman, S. A. et al., *J. Reproduct. Immunol.* 3:99, 1981; Heman A. et al., *Protides Biol. Fluids* 16:549, 1969). That homology and corresponding homologous reactivity of human IgM natural antibodies are firmly established here. The questions that may then arise concern the mechanism of tolerance for a set of natural antibodies reactive with a protein so ubiquitous in human tissues and the import of the loss of those antibodies, as well as the other distinctive sets of natural antibodies, in the course of HIV pathogenesis.

In the data presented below, the following methods were utilized.

METHODS

Preparation of SP80 Specimens of semen, obtained from clinically normal volunteer donors, were collected, allowed to liquefy, and pooled. Sperm-free plasma was obtained by centrifugation and separated by DEAE ion exchange chromatography (Friesen, H. S. et al., *J. Applied Biochem.* 3:164, 1981) into a pool of basic (above pH 7.8) and a pool of acidic fractions. Each pool was subjected to gel filtration (Sephacryl S 300 HR, Pharmacia Inc., Piscataway, N.J.); the first fraction of each pool was resolved at 80 kD and was designated SP80-acidic and SP80-basic, respectively. Lactoferrin (LF) from human milk was obtained from a commercial source (Sigma, St. Louis, Mo.).

Stain for Glycan was carried out by use of the Glycan Detection Kit (Boehringer Mannheim Corp.) utilizing oxidation with periodate, labelling with steroid hapten digitoxigenin and detection with an antibody-alkaline phosphatase conjugate.

Cyanogen bromide (CNBr) treatment of SP80-acidic, SP80-basic and LF were carried out as described for LF (Metz-Boutique, M. H. et al., *Eur. J. Biochem.* 145:659, 1984). Briefly, a 70% formic acid solution of the protein was incubated with CNBr (200-fold molar excess) in the dark for 18 hours at room temperature. Following lyophilization, the cleavage mixture was dissolved in sodium dodeoyl sulfate (SDS) and electrophoresed to display the pattern of cleavage fractions. For the second cleavage treatment of fraction 1, the fraction was cut out of the gel and an aqueous extract of the peptide fragments was subjected to a repetition of the CNBr treatment, extended to 48 hours.

Immunoreactivity. Immobilin P membrane (Millipore) transfers of the polyacrylamide gel electrophoresis (PAGE) of SP80 acidic, SP80 basic and LF were tested with (1) rabbit antiserum raised by immunization with purified SP80 followed by peroxidase labeled, affinity purified goat IgG anti-rabbit IgG (Tago) and (2) normal human serum followed by affinity purified rabbit IgG anti-human IgM, μ chain specific (Kirkegaard and Perry Inc.).

ELISA of human serum IgM reactivity with fraction 7 of SP80 (SP80 fr7) was carried out by protocols previously described (Rodman, T. C. et al., *Clin. Immunol. Immunopath.* 57:430, 1990; Rodman, T. C. et al., *J. Exp. Med.* 175:1247, 1992; Rodman, T. C. et al., *J. Immunol. Meth.* 94:105, 1986; Prusline F. H. et al., *J. Immunol. Meth.* 137:27, 1991). The plotted O.D. values (FIG. 7) are those of reactivity of serum 1:100 with 20 μg/ml SP80 fr7, with the O.D. value for "serum background" (serum 1:100, no antigen) subtracted. Each O.D. value is the mean of 2–5 separate assays. Each microtiter plate included both normal (HIV negative) and HIV positive sera.

Absorption of the SP80 fr7 reactive antibodies of human sera was carried out by use of CNBr activated SEPHAROSE® 4B resin (Pharmacia Inc.) Serum (1:100) was passed (by gravity) through columns of successive lengths containing SP80 fr7 bound to the resin: 400 μg protein/g resin. The three absorption columns were: 6 mm containing 0.1 g, 21 mm containing 0.3 g and 35 mm containing 0.5 g of SP80 fr7-bound resin. The flow through (absorbed serum) from each column was then tested by ELISA for separate reactivity with SP80 fr7 and the peptides containing the reactive sites of the two above previously characterized sets of natural IgM antibodies of human sera.

RESULTS

Figure 5:
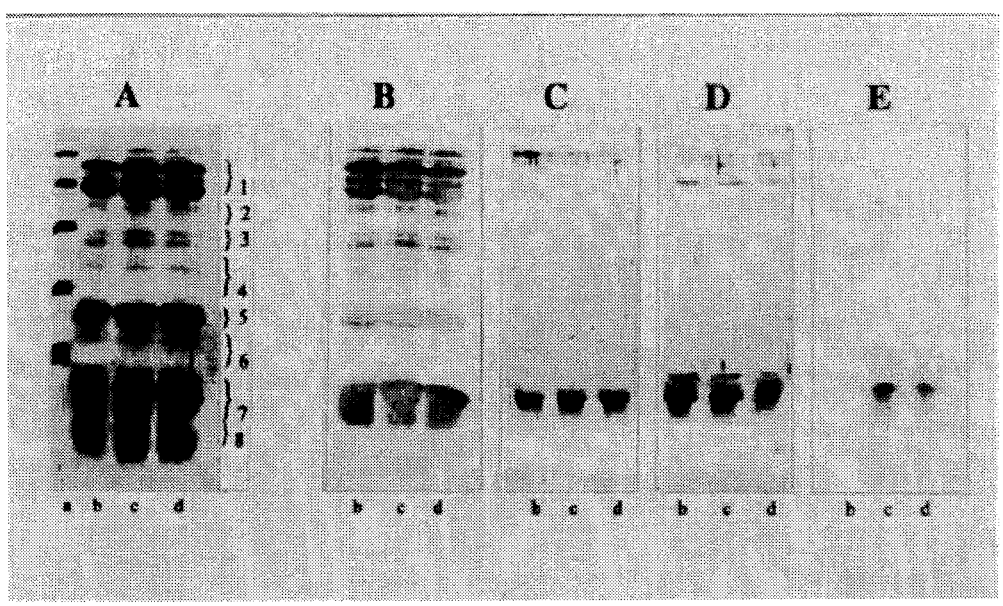
FIG. 5A—Fractions 1–8 of SP80 basic (lane b), SP80 acidic (lane c) and lactoferrin (LF) (lane d) obtained by cyanogen bromide (CNBr) cleavage. Protein stained PAGE showing molecular weight distribution (lane a: m.w. markers 66, 43, 30, 20, 14.4 kD) of the fractions and homology of cleavage patterns of LF and the two variants of SP80.
FIG. 5B—Fractions 1–8 of SP80 basic (lane b), SP80 acidic (lane c) and lactoferrin (LF) (lane d) obtained by cyanogen bromide (CNBr) cleavage. Immunotransfers with a rabbit serum raised against SP80 (acidic and basic) showing the polyvalency of the reactivity of the antiserum and the homology of reactivity of SP80 anti LF.
FIG. 5C—Fractions 1–8 of SP80 basic (lane b), SP80 acidic (lane c) and lactoferrin (LF) (lane d) obtained by cyanogen bromide (CNBr) cleavage. Immunotransfers with human sera (C male, D female) showing that the IgM reactivity of normal human sera is specifically localized in fractions 1 and 7.
FIG. 5E—Fractions 1–8 of SP80 basic (lane b), SP80 acidic (lane c) and lactoferrin (LF) (lane d) obtained by cyanogen bromide (CNBr) cleavage. Immunotransfers with human sera (C male, D female) showing that the IgM reactivity of normal human sera is specifically localized in fractions 1 and 7.
Figure 6:
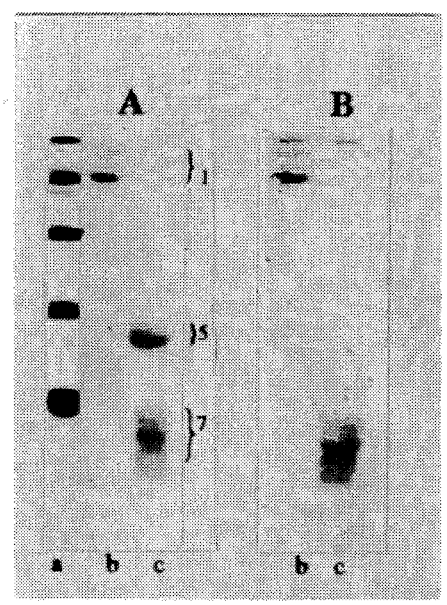
FIG. 6A—PAGE of fragments obtained by further CNBr digestion of fraction 1 of SP80 basic (FIG. 5A, lane b). Lane a, molecular weight markers (as for FIG. 5A); lane b, isolated fraction 1; lane c, cleavage fragments, showing that the components of fraction 1 are distributed to positions corresponding to fractions 5 and 7 (FIG. 5A) and, again, the serum IgM reactivity is restricted to that designated fraction 7, resolved at 10 kD.
FIG. 6B—IMMUNOTRANSFER of fragments obtained by further CNBr digestion of fraction 1 of SP80 basic (FIG. 5A, lane b). Lane a, molecular weight markers (as for FIG. 5A); lane b, isolated fraction 1; lane c, cleavage fragments, showing that the components of fraction 1 are distributed to positions corresponding to fractions 5 and 7 (FIG. 5A) and, again, the serum IgM reactivity is restricted to that designated fraction 7, resolved at 10 kD.

CNBr treatment of lactoferrin, SP80-acidic and SP80basic produced apparently identical cleavage patterns, separable into fractions 1 to 8 (FIG. 5A). Similar patterns of reactivity with a rabbit antiserum generated by immunization with SP80 were displayed by all fractions of each of the three proteins (FIG. 5B). Immunoreactivity with IgM of human sera was also displayed by the three proteins. However, in contrast to the reactivity displayed by the rabbit immune serum, the reactivity of the human sera, putatively due to a set of natural antibodies, was restricted to fractions 1 and 7 (FIGS. 5C,D). Further CNBr treatment of fraction 1 (FIGS. 6A and 6B) resulted in two fragments corresponding in position to fractions 5 and 7 of the original cleavage pattern (FIG. 5A) and, again, reactivity with human serum was demonstrated only with the fragment corresponding to fraction 7 (FIG. 5B). Apparently, therefore, fraction 1 obtained by the first CNBr treatment included the moiety of fraction 7 with which human serum IgM is reactive and that reactivity is specifically restricted to the peptide(s) segregated in fraction 7 of both LF and SP80.

Lactoferrin is composed of two closely homologous lobes each containing a single glycan side chain (Metz-Boutique, supra; Anderson, B. F. et al., *J. Mol. Biol.* 209:711, 1989). Since the carbohydrate stain was demonstrated only in fraction 7 following CNBr cleavage of LF and SP80 (FIG. 5E) it appears that both glycans as well as specific immunoreactivity with human serum IgM are congregated in fraction 7. Evidence that the immunoreactivity is not dependent upon the carbohydrate is provided by the data of FIGS. 5C,D, showing that the human sera are reactive with the SP80-basic as well as the LF and SP80-acidic.

Figure 7A:
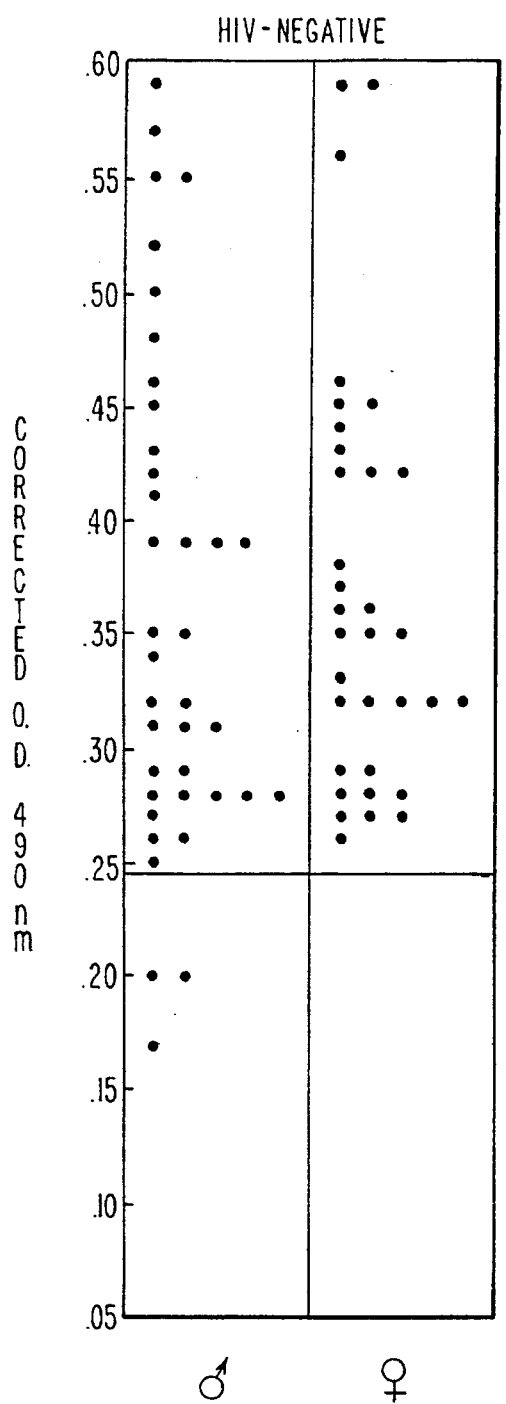
FIG. 7A—Distribution of O.D. values (titers) obtained by ELISA of reactivity of human serum IgM with SP80, 1:100 dilution of serum with 20 µg/ml of SP80 fr7. HIV negative sera from clinically normal males (n=38) and females (n=33).
Figure 7B:
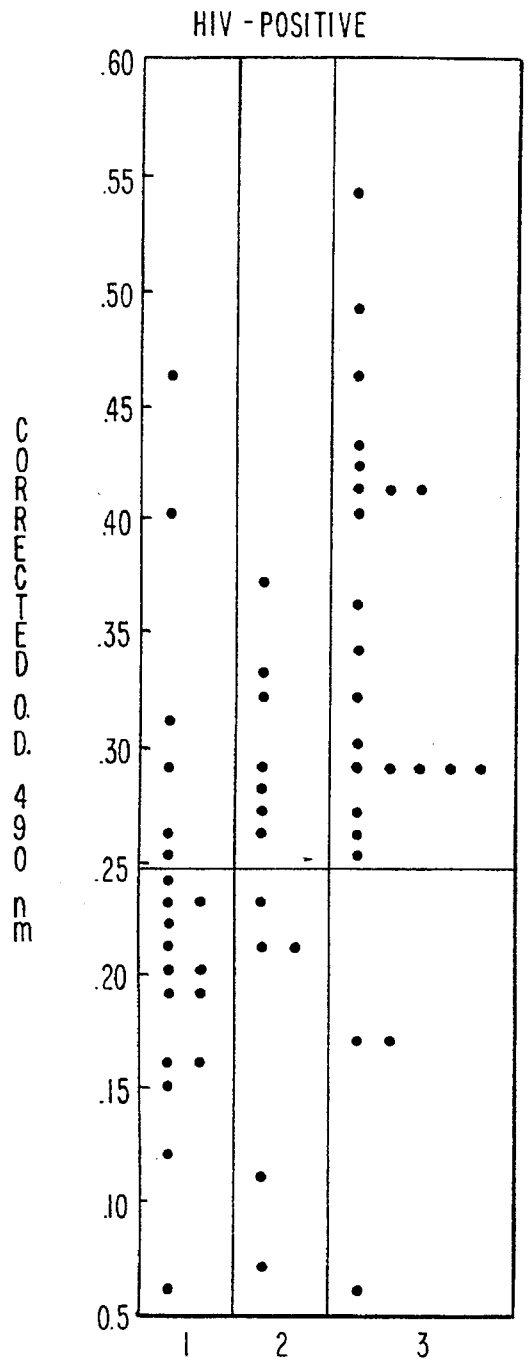

The data of FIGS. 7A and 7B show that IgM antibodies reactive with fraction 7 of SP80 are present, in a circumscribed range of titers, in normal HIV-negative sera. For HIV-positive sera, titers below the defined normal range are displayed by a progressively greater percentage of sera as imminence of diagnosis to AIDS progresses. Thus, while 3% of the 71 normal HIV-negative sera had titers below the designated lower limit of the normal range, 70% of those HIV-positive sera from patients diagnosed with AIDS or ARC at the time of specimen collection, 42% of those diagnosed within one year and 13% of those not meeting the criteria for diagnosis of AIDS within one year, had values below that limit.

Identification of the IgM antibodies of normal human serum reactive with one or more moieties of SP80 fr7, as a specific subset distinct from two subsets of IgM antibodies previously identified above (i.e. protamine and Tat amino acid residue Nos. 22–33) and designated as natural antibodies is provided by the data of FIGS. 8A–8C. Those data show that, following depletion of SP80 reactive antibodies by absorption, both HIV-positive and HIV-negative sera retain full reactivity with a peptide of HIV Tat and with a peptide of protamine, each of which includes an epitope previously shown to be recognized by a specific set of IgM antibodies.

Natural antibodies frequently have been characterized as low affinity. However, as noted previously, it is not feasible to measure the affinity constant of an individual set of antibodies in the polyvalent context of serum. Procedures were established to separately identify and assay a set of natural, low affinity antibodies reactive with an epitope of protamine homologous or identical with the epitope for a set of immune-induced, presumably high affinity, antibodies. The ontogenetic and molecular uniqueness of protamine, a DNA binding protein occurring only in spermatozoa, indicated that two such sets of antibodies reactive with protamine are present in normal adult sera. Upon the assumption that antibodies of low affinity do not bind appreciably at the low concentrations of immobilized antigen (e.g., as in the ELISA) at which antibodies of high affinity may bind, the reactivity curves of ELISA of IgM of sera with human protamine 2b and with constituent peptides of that protein, were examined. In accordance with that assumption, for virtually all normal sera examined, a sharp rise in slope of those curves were observed at the higher antigen concentrations. That rise was attributed to the reactivity of a lower affinity, but epitopically similar, subset of IgM antibodies. A formula was then devised for measuring the titer of antibodies represented by the increase in rise of slope. For that system, it was found empirically, that the lowest antigen concentration at which specific reactivity of serum at dilution of 1:500 was detected was 2 µg/ml and the change in slope was manifested by serum at dilution 1:100 in the range of antigen concentrations of 5 to 10 µg/ml. Therefore, the formula for derived O.D. of the low affinity subset was constructed:

When the Δ20–Δ2 formula derived initially from IgM reactive with protamines (or the affinity binding) was applied to IgM reactivity with SP80 fr7, similar evidence for a low affinity subset of those antibodies was presented (FIGS. 9A and 9B). Although the attrition of that subset for SP80 reactive IgM was not as marked as that of the protamine-reactive IgM, a circumscribed range of normal titers was evident and the percentage decrease in the HIV positive sera followed the progression of imminence to a diagnosis of AIDS (FIGS. 9A and 9B).

DISCUSSION

IgM antibodies reactive with lactoferrin and its seminal plasma homologue, SP80, are present in human sera. Following CNBr fractionation of the several variants of that protein, milk lactoferrin, SP80 glycosylated and SP80 non-glycosylated, the serum IgM reactivity was segregated in a single fraction, suggesting that the reactive site for the IgM antibodies is restricted to a specific sequence of the molecule. In contrast, reactivity with an immune serum, i.e. serum of a rabbit immunized with SP80, is displayed with all fractions of the cleaved protein. That distinction, together with detection of lactoferrin/SP80 reactive IgM antibodies in all sera of a set of clinically normal males and females within a limited range of titers, allows the designation of that set of human IgM as natural antibodies. In addition, those antibodies are depleted in the course of HIV infection and it has been confirmed that the lactoferrin/SP80 reactive antibodies are specific and non-cross reactive with two other distinct sets of natural antibodies identified above in normal sera and found to undergo that depletion.

Although not all of the biological functions and involvements of lactoferrin have been elucidated, its extensive occurrence in various cells and tissues, including blood plasma, is well established (Sanchez, L., et al., *Arch. Dis. Child.* 67:657, 1992) and its accessibility to circulating antibodies is clearly evident. Therefore, the determination that a set of IgM antibodies reactive with lactoferrin, and its seminal plasma homologue SP80, is present in all normal sera provokes questions as to the significance of those antibodies. With the current great expansion of interest in natural antibodies several new bodies of information, including concepts and data, have developed. In particular, the relationship between natural antibodies, i.e. those that arise independently of known immune induction, may be reactive with autoantigens but are nonpathogenic, and autoantibodies, i.e. those that are reactive with autoantigens and are known or suspected of being involved in pathogenic processes, has stimulated several new trends of conjecture and investigation (Algiman, N. et al. *Proc. Nat'l. Acad. Sci. USA* 89:3795, 1992; Turnano, A. et al. *Proc. Nat'l. Acad. Sci. USA* 89: 4447, 1992; Stein, R. et al. *Clin. Exp. Immunol.* 85:418, 1991; DeFranco, A. *Nature* 357:14, 1992). One such trend that may have relevance to the data presented herein of the attrition of natural antibodies following HIV infection concerns the potential role of natural antibodies in the equilibrium of the idiotypic network. Thus, perturbation of the network may be related—cause or effect—to the depletion of natural antibodies following HIV infection. That would be in line with current inquiry into a possible autoimmune component of the pathogenetic progression to AIDS (Wang, H. et al., *Eur. J. Immunol.*, in press, 1992; Veljkovic, V. et al. *Immunol. Today* 13:38, 1992; Hoffman, G. W. *Proc. Nat'l. Acad. Sci USA* 88:3060, 1991).

EXAMPLE 3: NATURAL IgM ANTIBODIES IMMUNOREACTION WITH A SECOND EPITOPE IN HIV TAT PROTEIN

As described above, three sets of natural IgM antibodies, each with highly specific epitopic reactivity (i.e., protamine, SP80 and HIV Tat protein amino acid residue Nos. 22–33) have been identified and the presence of significant titers of each in virtually all normal sera demonstrated and examined and the deficiency or absence of each in an increasingly greater percentage of HIV positive sera as imminence to AIDS progresses. The dichotomy of "present in HIV negative and deficient in HIV positive sera" was demonstrated for a set of IgM antibodies specifically reactive with HIV Tat the regulatory protein essential for HIV replication (Arya, S. K. et al., *Science* 229:69, 1985; Fisher, A. G. et al., *Nature* 320:367, 1986; Dayton, A. T. et al., *Cell* 44:941, 1986). Those antibodies, non-immune in origin and designated natural antibodies, were detected in all of the 66 normal, HIV negative sera reported (and in 20 subsequently examined). The titers of Tat-reactive IgM antibodies of 97% of those HIV-negative sera were within a circumscribed range. Of the HIV-positive sera examined, however, over 50% had titers of those antibodies that were below the normal range, with the greatest attrition, 66% below normal and 16% below the limit of detection, in sera of patients diagnosed with AIDS at specimen collection.

As described in Example 1 above, by use of a series of overlapping peptides representing the 1–82 amino acid sequence of HIV-Tat, a reactive site for the human IgM antibodies was localized to residues 22–33. In accordance with the high cysteine content of that sequence, the reactive site was found to be dependent upon a cys—cys conformed state. However, when the reactivity of each serum with total Tat protein (Recombinant HIV Tat, expressed in *E. coli*, was obtained from American Biotechnologies Inc., Cambridge, Mass.) and with peptide 22–33 were compared (Table 4), it was apparent that, for all HIV negative sera and a proportion of the HIV positive sera, the total Tat reactivity included a component in addition to that displayed by reactivity with peptide 22–33. Therefore, the possibility was presented that none of the 11 dodecapeptides of Tat (Table 1) employed to localize the IgM reactive site(s), although constructed with 5 residue overlaps, included the complete sequence for another natural antibody epitope. Presented below is the identification of another set of IgM natural antibodies reactive with another specific sequence of Tat (Table 5) and confirmation that those two sets of antibodies comprise the total Tat reactivity in HIV negative and HIV positive sera (Table 3). Particularly significant is the disclosure that the two epitopes recognized by the Tat reactive natural antibodies are coincident with the two sequences and specific residues of HIV Tat shown to be essential to Tat function (Cullen, B. R., *Cell* 63:655, 1990; Calnan, B. J. et al., *Genes Develop.* 5:201, 1991).

Consonant with the concept that natural antibodies may provide a "first line of defense" (Casali, P. et al., *Ann Rev. Immunol.* 2:513, 1989) against an infectious invader is the inference that such antibody mediated defense would imply reasonably specific recognition by the antibody for a component of the "invader". The data presented in Example 1 above showed that the epitope for a set of natural antibodies reactive with the invader HIV Tat, is specific and occurs within the cysteine-rich domain, which is one of the two sites of Tat found to mediate its function in transactivation of HIV RNA (Cullen, B. R., *Cell* 63:655, 1990; Calnan, B. J. et al., *Genes Develop.* 5:201, 1991). As disclosed in U.S. patent application Ser. No. 07/924,412, normal human sera contain a set of natural IgM antibodies reactive with protamine, an arginine-rich sperm-unique nuclear protein. The possibility that a specific epitope for another set of natural antibodies reactive with HIV Tat might be embodied within the other designated functional site, the basic arginine-rich domain, was investigated.

Although some differences in experimental approach and interpretation have arisen concerning the significance of each domain or residue in Tat function, the consensus appears to include the following: 1. the cysteine-rich domain is essential for Tat function, possibly through conformational and dimerization effects (Frankel, A. D. et al., *Science* 240:70, 1988; Dadaie, M. R. et al., *Proc. Natl. Acad. Sci. USA* 85:9224, 1988; Garcia, J. A. et al., *EMBO J.* 7:3143, 1988; Rice, A. P. et al., *J. Virol.* 64:1864, 1990; Jeyapaul, J. et al., *Proc. Natl. Acad. Sci. USA* 87:7030, 1990); 2. the principle steps in transactivation of HIV RNA, however, are mediated through the basic domain (Cullen, B. R., *Cell* 63:655, 1990; Calnan, B. J. et al., *Genes Develop.* 5:201, 1991); 3. although over-all charge and number of arginines are significant, specific arginine residues are essential (Mann, D. A. et al., *EMBO J.* 10:1733, 1991; Kamine, J. et al., *Virology* 182:570, 1991; Puglisi, J. D. et al., *Science* 257:76, 1992); 4. a large body of point mutation studies has established that all 6 arginines participate (Weeks, K. M. et al., *Science* 249:1281, 1990; Subramanian, T. et al., *EMBO J.* 10:2311, 1991; Calnan, B. et al., *Science* 252:1167, 1991; Tao, J. et al., *Proc. Natl. Acad. Sci. USA* 89:2723, 1992), but arginine at position 49 is specifically significant for binding of Tat to TAR, the target sequence of HIV RNA (Cordingly, M. D. et al., *Proc. Soc. Natl. Acad. Sci. USA* 87:8985, 1990; Delling, U. et al., *Proc. Natl. Acad. Sci. USA* 88:634, 1991).

Inspection of the 11 peptides (Table 1 above) used for the previous study of Tat reactivity with IgM of human serum revealed that none included all 6 of the arginine residues within the basic domain of 49–59 (Rodman, T. C. et al., *J. Exp. Med.* 175:1247, 1992). Peptide 50–61 (#8, Table 1), which includes the arginine triplet, the arginine doublet and the lysine doublet, but lacks arg 49, showed barely significant reactivity with 2 of 24 human sera tested. Therefore, another 12 residue, sequence-faithful peptide of Tat was constructed, residues 48–59 (SEQ ID. NO:12), Table 5), which includes arg 49, as well as all of the other arginines of the basic domain. Upon testing by ELISA of human serum IgM, with each of the peptides of Tat, now totalling 12, significant reactivity was revealed with, as before, peptide 22–33, with the new peptide, 48–59, and with none other (Table 5). The data of Table 5 provide assurance that the reactivity with those two peptides comprises the total reactivity with HIV Tat, in both HIV positive and HIV negative sera. As shown, absorption of a serum from each of the three groups, HIV negative, HIV positive (latency) and HIV positive (AIDS) on peptide 22–33 and 48–59, consecutively, removed all IgM reactivity with total Tat (Table 6 and FIGS. 11A and 11B). Additional absorption studies firmly establish the separate identities of the epitopes for each of those two sets of antibodies (Table 6, FIGS. 10A, 10B, 11A and 11B).

As has been demonstrated above, there exists a high level of epitopic specificity of 3 sets of natural antibodies: the above noted cysteine-rich sequence of Tat, a 10 kDa fragment of the 80 kDa glycoprotein, lactoferrin and the repetitive arginine-rich sequences of protamine and the separate epitope for each set has been defined. The question of whether the set of IgM antibodies reactive with the arginine rich Tat peptide 48–59 is the same set that is reactive with protamine was addressed, also, by absorption procedures (Table 6 and FIGS. 11A and 11B). The data of Table 6 and FIGS. 11A and 11B affirm that the set of antibodies reactive with Tat 48–59 is not reactive with Tat 22–33, but that it is reactive with the two protamine-derived peptides, Pp1 and Pp2 (The protamine peptides, each representing a 12 residue sequence of human protamine 2b (McKay, D. J. et al., *Eur. J. Biochem.* 156:5, 1986) were synthesized by the Rockefeller University Protein Sequencing Service and amino acid content verified by the Mass Spectrometric Biotechnology Resource of Rockefeller University. Pp1 (residues 33–44 (SEQ. ID. NO:13)) SCRHRRRHRRGC; Pp2 (residues 24–35 (SEQ. ID. NO:14) RCCRRRKRRSCR). The reactivity of each of the two protamine peptides is reciprocally and totally absorbed by the other. Absorption by Tat 48–59 however, removes part, but not all, of the reactivity of the protamine peptides, Pp1 and Pp2 (Table 6 and FIGS. 11A and 11B).

By use of CNBr activated sepharose 4B resin (Pharmacia Inc.) to which the peptide was bound (400 μg peptide/g resin); the use of progressively longer, narrow (1 cm.) columns assures complete specific absorption and minimal non-specific (by the resin) absorption. As shown in Table 6 and FIGS. 11A and 11B, serum absorbed on the longer columns of Tat 48–59-bound resin was devoid of Tat 48–59 reactive antibodies, but lost none of its complement of Tat 22–33 reactive antibodies. The absorption procedure assures that the incomplete absorption of the protamine peptide reactivity by Tat 48–59 is not due to experimental methodology, e.g., inadequate contact of serum IgM with the absorption matrix.

The data of FIGS. 10A and 10B reiterate that the protamine peptide reactive IgM of a normal HIV negative serum includes two subsets differing in affinity for antigen. The IgM reactivities of both the HIV negative and the HIV positive sera with Tat 48–59 appear to be relatively homogenous with respect to affinity (FIG. 10). Following absorption on the Tat peptide 48–59, the reactivity of the HIV negative serum with each of the two protamine peptides shows decline, but is not abolished (FIG. 10). Analysis of the decline indicates that it reflects deletion of the low affinity subset of the protamine-reactive IgM, manifested by the change in slope of the curves for the higher antigen concentrations. For the HIV positive (AIDS) serum which displays a low titer of the natural low affinity subset of protamine reactive antibodies (FIGS. 10A and 10B), there is no decline in reactivity with the protamine peptides or change in slope of the curves, following absorption on Tat 48–59. Therefore, the set of IgM antibodies reactive with Tat 48–59 is reactive, also, with the protamine peptides, but that reactivity corresponds specifically to the low affinity subset of protamine reactive IgM, designated the natural antibody subset. Therefore, the Tat 48–59 reactive IgM antibodies appear to be characteristically and exclusively identifiable as a set of natural antibodies.

TABLE 3

Percentage distribution of ratios of O.D. values, by ELISA of IgM of three groups of sera: *O.D. Total Tat* (Rodman, T. C. et al., *J. Exp. Med.* 175:1247, 1992); The O.D. values are those for ELISA of serum 1:100 with 10 μg/ml, by the procedure described (Rodman, T. C. et al., *J. Exp. Med.* 167:1228, 1988; Rodman, T. C. et al., *Clin. Immunol. Immunopathol.* 57:430, 1990; Rodman, T. C. et al., *J. Exp. Med.* 175:1247, 1992; Rodman, T. C. et al., *Abstr. PoA* 2429, *VIII Internatl. Conf. AIDS*, 1992; Rodman, T. C. et al., submitted). Since equivalent weights of the total Tat protein (Recombinant HIV Tat, expressed in *E. coli*, was obtained from American Biotechnologies Inc., Cambridge, Mass.) and the 12 residue peptide 22–33 were used, equal or higher O.D. values for the total protein indicates that a reactive site, other than that of peptide 22–33, is present in the total protein (Rodman, T. C. et al., *J. Exp. Med.* 175:1247, 1992). The O.D. values are those for ELISA of serum 1:100 with 10 ug/ml, by the procedure described (Rodman, T. C. et al., *J. Exp. Med.* 167:1228, 1988; Rodman, T. C. et al., *Clin. Immunol. Immunopathol.* 57:430, 1990; Rodman, T. C. et al., *J. Exp. Med.* 175:1247, 1992; Rodman, T. C. et al., *Abstr. PoA* 2429, *VIII Internatl. Conf. AIDS*, 1992; Rodman, T. C. et al., submitted). Since equivalent weights of the total Tat protein (Recombinant HIV Tat, expressed in *E. coli*, was obtained from American Biotechnologies Inc., Cambridge, Mass.) and the 12 residue peptide 22–33 were used, equal or higher O.D. values for the total protein indicates that a reactive site, other than that of peptide 22–33, is present in the total protein.

TABLE 3

| | O.D. Tat 22–33 | | |
|---|---|---|---|
| | | % of sera | |
| range of ratio values | <1.0 | 1.1–2.0 | >2.0 |
| HIV negative (n = 40) | 0 | 67.5 | 32.5 |
| HIV positive, AIDS within one year (n = 32) | 31 | 44 | 25 |
| HIV positive, latency (n = 18) | 11 | 39 | 50 |

These data indicate that all normal HIV negative sera contain Tat reactive IgM antibodies in addition to the set reactive with peptide 22–33, identified above as Example 1. 31% of HIV positive sera from AIDS patients and 11% from HIV positive asymptomatic (latency) patients appear to lack that "other" set, whereas 50% of the latter group display a disproportionately high titer of that set of IgM antibodies. The data of this Example identify the epitope for the "other" set of Tat reactive antibodies within residues 48–59 and suggest that those IgM natural antibodies may represent a host factor contributing to maintenance of the state of latency.

TABLE 4

O.D. (490 nm) values for ELISA of HIV positive and HIV negative sera with each of the 12 dodecapeptides of Tat (25—All peptides were constructed on the basis of Tat sequence noted in: Frankel, A. D. et al., *Proc. Soc. Acad. Sci. USA* 86:7397, 1989. Peptides were synthesized and sequences verified by Multiple Peptide Systems (San Diego, Calif.) and amino acid content verified by the Mass Spectrometric Biotechnology Resource of the Rockefeller University, under the direction of Dr. Brian T. Chait). Assay of other representative sera with peptides 1–11, reported previously (Rodman, T. C. et al., *J. Exp. Med.* 175:1247, 1992), showed reactivity only with peptide #4. These data show reactivity by all sera with, as before, peptide #4, and also with peptide #12, constructed for this study to include all residues of the basic sequence shown to be essential for Tat function (Cullen, B. R., *Cell* 63:655, 1990; Calnan, B. J. et al., *Genes Develop.* 5:201, 1991; Mann, D. A. et al., *EMBO J.* 10:1733, 1991; Kamine, J. et al., *Virology* 182:570, 1991; Puglisi, J. D. et al., *Science* 257:76, 1992; Weeks, K. M. et al., *Science* 249:1281, 1990; Subramanian, T. et al., *EMBO J.* 10:2311, 1991; Calnan, B. et al., *Science* 252:1167, 1991; Tao, J. et al., *Proc. Natl. Acad. Sci. USA* 89:2723, 1992; Cordingly, M. G. et al., *Proc. Soc. Natl. Acad. Sci. USA* 87:8985, 1990; Delling, U. et al., *Proc. Natl. Acad. Sci. USA* 88:634, 1991). The low levels of reactivity of the HIV positive sera with peptide #12, residues 48–59, is in accordance with previous demonstrations of deficiency of specific sets of natural antibodies in HIV positive sera (Rodman, T. C. et al., *Clin. Immunol. Immunopathol.* 57:430, 1990; Rodman, T. C. et al., *J. Exp. Med.* 175:1247, 1992; Rodman, T. C. et al., *Abstr. PoA* 2429, *VIII Internatl. Conf. AIDS*, 1992; Rodman, T. C. et al., submitted).

TABLE 4

A. HIV-1 Tat Protein

MEPVDPRLEPWKHPGSQPKTACTNCYCKKCCFHCQVCFITAKALGISYGRKKRRQRRRPPQGSQTHQVSLSKQPTSQSRGDPT (SEQ. ID. NO:15)

| Tat peptide | Residues | Sequence |
|---|---|---|
| 1 | 1–12 | MEPVDPRLEPWK |
| 2 | 8–19 | LEPWKHPGSQPK |
| 3 | 15–26 | GSQPKTACTNCY |
| 4 | 22–33 | CTNCYCKKCCFH |
| 5 | 29–40 | KCCFHCQVCFIT |
| 6 | 36–47 | VCFITKALGISY |
| 7 | 43–54 | LGISYGRKKRRQ |
| 8 | 50–51 | KKRRQRRRPPQG |
| 9 | 57–68 | RPPQGSQTHQVS |
| 10 | 64–75 | THQVSLSKQPTS |
| 11 | 71–82 | KQPTSQSRGDPT |

TABLE 4-continued

| | 12 Protamine peptides | 48–59 | GRKKRRQRRRPP |
|---|---|---|---|
| | Pp1 | 33–44 | SCRHRRRHRRGC |
| | Pp2 | 24–35 | PSCRRRKRRSCR |

B. Reactivity with Human Serum IgM

| | HIV negative | | | | | | HIV positive | | | | | |
|---|---|---|---|---|---|---|---|---|---|---|---|---|
| | ♀ | | | ♂ | | | Latency | | | AIDS | | |
| Total Tat Protein | .69 | .45 | .65 | .64 | .45 | .55 | .38 | .27 | .40 | .27 | .22 | .16 |
| Tat peptide 4 | .48 | .30 | .31 | .39 | .30 | .29 | .30 | .25 | .31 | .20 | .16 | .12 |
| Tat peptide 12 | .22 | .18 | .21 | .28 | .19 | .27 | .13 | .10 | .14 | .13 | .11 | (.06) |
| Pp1 | .41 | .40 | .53 | .51 | .37 | .38 | .39 | .21 | .18 | .20 | .18 | .26 |
| Pp2 | .49 | .38 | .57 | .47 | .35 | .52 | .36 | .15 | .24 | .22 | .21 | .21 |

O.D. (490 nm) of serum reactivity with Tat and with each of the peptides, Tat 22–33 and Tat 48–59, pre and post absorption (18 Absorption of serum antibodies reactive with each of the peptides was carried out by use of CNBr activated sepharose 4B resin (Pharmacia Inc.) to which the peptide was bound (400 ug peptide/g resin). The use of progressively longer, narrow (1 cm.) columns assures complete specific absorption and minimal non-specific (by the resin) absorption. As shown in Table 6, serum absorbed on the longer columns of Tat 48–59-bound resin was devoid of Tat 48–59 reactive antibodies, but lost none of its complement of Tat 22–33 reactive antibodies). All reactivity with Total Tat was deleted following absorption on the two peptides, consecutively.

TABLE 5

| | HIV negative | | HIV positive (latency) | | HIV positive (AIDS) | |
|---|---|---|---|---|---|---|
| | pre | post | pre | post | pre | post |
| Total Tat (1–84) | .79 | .05 | .49 | .06 | .29 | .05 |
| Tat 22–33 | .26 | .04 | .17 | .03 | .26 | .03 |
| Tat 48–59 | .30 | .04 | .14 | .04 | .14 | .04 |

TABLE 6

% Depletion of Reactivity with Each Peptide Following Absorption

| | | Absorption Columns | | | | | | | |
|---|---|---|---|---|---|---|---|---|---|
| | | Tat 48–59 | | Tat 22–33 | | Pp1 | | Pp2 | |
| serum | peptide | 30 mm | 60 mm | 30 mm | 60 mm | 30 mm | 60 mm | 30 mm | 60 mm |
| HIV neg. | Tat48–59 | 66 | 100 | 0 | 0 | 50 | 98 | 100 | 100 |
| | Tat22–33 | 0 | 0 | 100 | 100 | 0 | 0 | 0 | 0 |
| | Pp1 | 66 | 73 | 0 | 0 | 100 | 100 | 81 | 97 |
| | Pp2 | 70 | 72 | 0 | 0 | 84 | 98 | 80 | 98 |
| HIV Pos. latency | Tat48–59 | 38 | 100 | 0 | 0 | | | | |
| | Tat22–33 | 0 | 0 | 100 | 100 | | | | |
| | Pp1 | 59 | 66 | | | | | | |
| | Pp2 | 55 | 53 | | | | | | |
| HIV Pos. AIDS | Tat48–59 | 26 | 100 | | | | | | |
| | Tat22–33 | 0 | 0 | | | | | | |
| | Pp1 | 0 | 0 | | | | | | |
| | Pp2 | 0 | 0 | | | | | | |

Absorption on Tat 22–33 depleted, from all sera, all reactivity with that peptide and none of the reactivity with Tat 48–59, or with the protamine-derived peptides, Pp1 and Pp2. (The protamine peptides, each representing a 12 residue sequence of human protamine 2b (McKay, D. J. et al., Eur. J. Biochem. 156:5, 1986) were synthesized by the Rockefeller University Protein Sequencing Service and amino acid content verified by the Mass Spectrometric Biotechnology Resource of Rockefeller University; Pp1 (residues 33–44) SCRHRRRHRRGC, Seq. ID 13, Pp2 (residues 24–35 Seq. ID 14 ), RCCRRRKRRSCR.). Absorption on Tat 48–59 depleted none of the reactivity with Tat 22–33, all of the reactivity with Tat 48–59, and part of the reactivity with each, Pp1 and Pp2. Each of those protamine peptides absorbed total reactivity of the other.

EXAMPLE 4: ISOLATION OF THE NATURAL IgM ANTIBODIES

Pooled normal plasma, available from and certified by the New York Blood Center will be obtained. The plasma will be depleted of albumin by cold ethanol precipitation, and the IgG content depleted or greatly diminished by absorption on protein G agarose (Genex). By use of an FPLC sizing column (Sepharose 6, Pharmacia), a fraction of proteins of molecular weight $5 \times 10^6 – 5 \times 10^3$ which will include IgG, IgA and small IgM will be obtained. (Procedures for exclusion of IgA are under study. As noted in the Sandoglobin leaflet blood products containing IgA "are contraindicated in patients with selective IgA deficiency, who possess antibodies to IgA". Therefore, if possible, absolute exclusion of IgA should be carried out).

The resulting product should provide a fraction of normal immunoglobulins greatly enriched in small IgM's and, expectedly, in Tat reactive IgM antibodies. If testing of that fraction shows titers of Tat peptide 12 reactive antibodies, greatly enhanced over those depicted in Table 7 below, that product will comprise a useful pharmaceutical product and a useful additive to IVIG for treatment of HIV infected individuals.

EXAMPLE 5: IVIG CONTAINS NATURAL IgM ANTIBODIES

IVIG intravenous immunoglobulin) therapy has been in practice for a number of years. That consists of intravenous administration of a preparation of the IgG fraction separated and purified from pooled normal plasma. A number of proprietary pharmaceutical products for IVIG are available. It has been established that IVIG is clinically beneficial for both pediatric and adult HIV infected patients. In fact, its effective in treatment of pediatrics resulted in issuance, in mid-1991 of an advisory "for immediate release" by NICHHD that the monthly administration IVIG for HIV infected pediatrics had demonstrated "efficacy and safety" and its use was urged.

As noted, prior to the HIV epidemic, IVIG administration was in use in treatment of various diseases believed to have autoimmune basis. A large volume of reports include discussions and speculations regarding the possible mechanics of the beneficial effect. The dominant and very credible concept is that of restoration of idiotypic network(s) by provision of key antibodies that have been depleted in the disease process. Since IVIG preparations are derived from a pool of a large number of donors, the expectation is reasonable that "missing" antibodies of various allotypes as well as specificities will be provided.

The efficacy of IVIG in delaying the progression of HIV may, in addition to restoration of the idiotypic network, be due to replacement of the IgM natural antibodies shown to be depleted in sera of HIV positive patients, as the definitive state of AIDS is neared.

The descriptions of the various IVIG's as concentrates of IgG from pooled plasma suggests that fractionation by size is included in the methods. Accordingly, the following data demonstrating the presence of specific IgM antibodies in each of 3 commercial IVIG preparations that have been tested, suggest that those IgM's may be smaller than the conventional pentavalent IgM. The data clearly show that the IgM antibodies reactive with the Tat protein of HIV, which have been identified as present in normal, HIV negative sera and have characterized as natural antibodies, are clearly present in 2 of the 3 commercial IVIG preparations and may be present in the 3rd.

The IVIG products tested were:

| | | |
|---|---|---|
| 1. | Gamimmune N (Miles Inc., Cutter Biological) | |
| 2. | Sandoglobin (Sandoz Pharmaceuticals) prep 1 | |
| | Sandoglobin (Sandoz Pharmaceuticals) prep 2 | |
| | (prep 1 and prep 2 differ only in that they were received a month apart, and may represent different lots) | |
| 3. | Gammar IV (Armour Pharmaceutical Co.) | |

Each IVIG preparation was assayed (undiluted) by ELISA for IgM against the following antigen (each antigen at 10 μg/ml). Two normal sera, dilution 1:100, were assayed at the same time, on the same plate. All determinations were carried out in triplicate. The values listed in TABLE 7 below represent the mean of three determinations and the composite mean of three separate assays, each carried out independently.

Antigens

1. Tat protein (recombinant in *E. coli*, American Biotechnologies Inc. )
2. peptide 4 of Tat (C T N C Y C K K C C F H)
3. peptide 12 of Tat (G R K K R R Q R R R P P)
4. protamine peptide (Pp1) (S C R H R R R H R R G C)

It has been demonstrated above that IgM reactivity with each of those antigens in all HIV negative sera tested (n=84) and have shown that the low affinity subset of IgM reactive with Pp1, the IgM reactive with Tat protein and the IgM reactive with Tat peptide 12 decline in HIV positive sera. The IgM antibodies reactive with Tat peptide 12 constitute the same set of natural antibodies identified as the low affinity, protamine-reactive subset.

TABLE 7

| | Tat Protein | Tat Peptide | Tat Peptide 12 | Pp1 |
|---|---|---|---|---|
| normal serum ♂ | 53 | 45 | 22 | 58 |
| normal serum ♀ | 60 | 34 | 23 | 48 |
| Gamimmune N | 21 | 17 | 17 | 14 |
| Sandoglobin (1) | 31 | 06 | 11 | 05 |
| Sandoglobin (2) | 28 | 06 | 11 | 07 |
| Gammar IV | 30 | 06 | 08 | 04 |

The data of TABLE 7 are consistent with previous observations indicating that, in normal sera the IgM reactivity with Tat protein represents the composite reactivity with Tat peptide 12 represents part of the reactivity with Pp1. Analysis of those data indicated that the portion of the Pp1 reactivity represented by the reactivity of serum IgM with Tat peptide 12 is that of the low affinity, natural antibody subset of the protamine reactive IgM.

The data of TABLE 7 show that the low, but significant, titers of Tat peptide 12 reactivity of Gamimmune N and Sandoglobin are equivalent to or greater than the reactivity with Pp1. Those data indicate that the Tat peptide 12 reactive IgM (synonymous with the low affinity natural protamine reactive IgM) is present in this IVIG, but the other subset of protamine-reactive IgM, considered to be conventional, induced antibodies, is not present in the IVIG's. That interpretation is extended to postulate that the natural antibody IgM may be small (divalent), thus have segregated with the IgG fraction, while the characteristically pentavalent, induced IgM antibodies have been size-excluded from the IVIG.

That reasoning indicates that the Gammar IV IVIG preparation does not contain the subset of natural IgM antibodies in significant titer (O.D.>0.1 considered significant). All three IVIG preparations (TABLE 7) include IgM reactive with Tat protein. Since Gammar IV displayed no reactivity with Tat peptide 12 or Tat peptide 4, that datum represents an anomaly that requires further study.

Note: The specification and instructional leaflets for Sandoglobin and Gamimmune N state that the respective IVIG product includes "traces" of IgM. That statement is not included in the leaflet for Gammar IV.

The Tat reactive IgM antibodies present in at least some commercial IVIG products may be related to the reported, well documented, efficacy of those products in treatment of HIV infected individuals, particularly pediatrics.

That relationship would be in accord with the above inferences that IgM natural antibodies, particularly that set identified as the low affinity protamine-reactive and Tat peptide 12 reactive, are present in virtually all normal HIV negative sera and absent or deficient in HIV positive sera in increasing frequency as AIDS nears.

As has been shown above, the Tat peptide 12 reactive antibodies have a highly specific epitope requirement, and that the specific epitope is coincident with the sequence of HIV-1 Tat protein in which the key functional site, the basic region, of Tat is embodied. A well established function of HIV Tat is that of nuclear localization and RNA binding with consequent transactivation and viral replication. Therefore, the presence of Tat-reactive antibodies in plasma of HIV infected individuals may inactivate plasma-borne HIV Tat and thereby impede HIV replication. The presence of those antibodies in sera of asymptomatic or mildly symptomatic HIV positive individuals and their decline in individuals diagnosed as ARC or AIDS, is in accord with that hypothesis. Similarly, the presence of those Tat reactive antibodies in IVIG preparations may be related to the beneficial effects of IVIG administration to individuals (pediatric and adult) in the clinically latent period of HIV infection.

What is claimed is:

1. An isolated human natural IgM antibody immunoreactive with an epitope present on the HIV-1 Tat protein having the amino acid sequence SEQ ID NO:4, wherein said antibody is isolated from normal non-HIV-1 infected humans.

* * * * *